United States Patent
Bose et al.

(10) Patent No.: US 10,092,657 B2
(45) Date of Patent: Oct. 9, 2018

(54) OPSONIZED β-GLUCAN PREPARATIONS AND METHODS

(75) Inventors: Nandita Bose, Plymouth, MN (US); Anissa S. H. Chan, Arden Hills, MN (US)

(73) Assignee: Biothera, Inc., Eagan, MN (US)

( * ) Notice: Subject to any disclaimer, the term of this patent is extended or adjusted under 35 U.S.C. 154(b) by 278 days.

(21) Appl. No.: 14/123,624

(22) PCT Filed: Jun. 1, 2012

(86) PCT No.: PCT/US2012/040435
§ 371 (c)(1),
(2), (4) Date: Dec. 3, 2013

(87) PCT Pub. No.: WO2012/167061
PCT Pub. Date: Dec. 6, 2012

(65) Prior Publication Data
US 2014/0105935 A1    Apr. 17, 2014

Related U.S. Application Data

(60) Provisional application No. 61/493,101, filed on Jun. 3, 2011.

(51) Int. Cl.
| | |
|---|---|
| *C07H 1/00* | (2006.01) |
| *A61K 47/48* | (2006.01) |
| *A61K 31/716* | (2006.01) |
| *A61K 47/61* | (2017.01) |
| *A61K 47/64* | (2017.01) |

(52) U.S. Cl.
CPC ........ *A61K 47/4823* (2013.01); *A61K 31/716* (2013.01); *A61K 47/61* (2017.08); *A61K 47/64* (2017.08)

(58) Field of Classification Search
None
See application file for complete search history.

(56) References Cited

U.S. PATENT DOCUMENTS

| | | | | |
|---|---|---|---|---|
| 5,817,643 | A * | 10/1998 | Jamas | C08B 37/0024 |
| | | | | 514/54 |
| 6,294,321 | B1 | 9/2001 | Wakshull et al. | |
| 7,981,447 | B2 | 7/2011 | Cox | |
| 9,610,303 | B2 | 4/2017 | Magee et al. | |
| 2004/0014715 | A1 | 1/2004 | Ostroff | |
| 2008/0103112 | A1 | 5/2008 | Magee et al. | |
| 2011/0045049 | A1 * | 2/2011 | Rubin-Bejerano | A61K 8/73 |
| | | | | 424/423 |
| 2011/0177532 | A1 * | 7/2011 | Rubin-Bejerano | A61K 47/4823 |
| | | | | 435/7.92 |

FOREIGN PATENT DOCUMENTS

| | | |
|---|---|---|
| WO | WO 2012/154680 A2 | 11/2012 |
| WO | WO 2012/167061 A1 | 12/2012 |

OTHER PUBLICATIONS

Elstad et al. 'CD11b/CD18 integrin and a beta-glucan receptor act in concert to induce the synthesis of platelet-activating factor by monocytes.' J. Immuno. 152(1):220-230, 1994.*
Patent Application No. PCT/US2012/040435, filed Jun. 1, 2012; International Preliminary Report on Patentability dated Dec. 19, 2013; 7 pages.
Patent Application No. PCT/US2012/040435, filed Jun. 1, 2012; International Search Report / Written Opinion dated Sep. 28, 2012; 9 pages.
Patent Application No. EP 12793220.0, filed Jun. 1, 2012; Extended European Search Report dated Feb. 18, 2015; 7 pages.
Adams et al., "Differential High-Affinity Interaction of Dectin-1 with Natural or Synthetic Glucans Is Dependent upon Primary Structure and Is Influenced by Polymer Chain Length and Side-Chain Branching", *J Pharmacol Exp Ther.*, Apr. 2008; 325(1):115-123.
Bailey, "The Reaction of Pentoses with Anthrone", *Journal of Biological Chemistry*, 1958; 68:669-672.
Boxx et al., "Influence of Mannan and Glucan on Complement Activation and C3 Binding by *Candida albicans*", *Infect Immun.*, Mar. 2010; 78(3):1250-1259.
Brown et al., "Immune recognition: A new receptor for β-glucans", *Nature*, Sep. 6, 2001; 413:36-37.
Brown et al., "Dectin-1 is a Major β-Glucan Receptor on Macrophages", *J Exp Med.*, Aug. 5, 2002; 196(3):407-12.
Brown et al., "Fungal β-glucans and Mammalian Immunity", *Immunity*, Sep. 2003; 19:311-315.
Brown, "Dectin-1: a signalling non-TLR pattern-recognition receptor", *Nat Rev Immunol.*, Jan. 2006; 6(1):33-43.
Cai et al., "Energetics of Leukocyte Integrin activation", *J Biol Chem.* Jun. 16, 1995; 270(24):14358-14365.
Cain et al., "Role of Complement Receptor Type Three and Serum Opsonins in the Neutrophil Response to Yeast", *Complement*, 1987; 4(2):75-86.
Cheson et al., "The role of complement and IgG on zymosan opsonization", *Int Arch Allergy Appl Immunol.*, 1981 66(1):48-54.
Chiani et al., "Anti-β-glucan antibodies in healthy human subjects", *Vaccine*, Jan. 22, 2009; 27(4):513-519. Epub Nov. 27, 2008.

(Continued)

*Primary Examiner* — Nora M Rooney
(74) *Attorney, Agent, or Firm* — Mueting, Raasch & Gebhardt, P.A.

(57) ABSTRACT

Described herein are compositions that include isolated opsonized soluble β-glucan, methods of making those compositions and methods of using those compositions.

9 Claims, 10 Drawing Sheets

Specification includes a Sequence Listing.

(56) References Cited

OTHER PUBLICATIONS

Cleary et al., "The effect of molecular weight and β-1,6-linkages on priming of macrophage function in mice by (1,3)-β--D--glucan", *Immunol Cell Biol.*, Oct. 1999; 77(5):395-403.

Czop et al., "Properties of glycans that activate the human alternative complement pathway and interact with the human monocyte β-glucan receptor", *J. Immunol.*, Nov. 1985; 135(5):3388-3393.

Deimann et al., "Hepatic granulomas induced by glucan. An ultrastructural and peroxidase-cytochemical study", *Lab Invest.*, Aug. 1980; 43(2):172-181.

Des Prez et al., "Function of the Classical and Alternate Pathways of Human Complement in Serum Treated with Ethylene Glycol Tetraacetic Acid and $MgCl_2$-Ethylene Glycol Tetraacetic Acid", *Infect Immun.*, Jun. 1975; 11(6):1235-1243.

Dransfield et al., "Interaction of Leukocyte Integrins with Ligand Is Necessary but Not Sufficient for Function", *J Cell Biol.*, Mar. 1992; 116(6):1527-1535.

Ezekowitz et al., "Interaction of Human Monocytes, Macrophages, and Polymorphonuclear Leukocytes with Zymosan In Vitro: Role of Type 3 Complement Receptors and Macrophage-derived Complement", *J Clin Invest.*, Dec. 1985; 76(6):2368-2376.

Fearon et al., "Activation of the alternative complement pathway due to resistance of zymosan-bound amplification convertase to endogenous regulatory mechansims", *Proc. Natl. Acad. Sci. U.S.A.*, Apr. 1977; 74(4):1683-1687.

Gadjeva et al., "The Covalent Binding Reaction of Complement Component C3", *J Immunol.*, Jul. 15, 1998; 161(2):985-990.

Götze et al., "The c3-activator system: an alternate pathway of complement activation", *J Exp Med.*, Sep. 1, 1971; 134(3):90-108.

Hermanson, Chapter 2, "The Chemistry of Reactive Functional Groups", *Bioconjugate Techniques*, Academic Press, Waltham, Massachusetts; 1996. Title page, publisher's page, and pp. 137-166.

Hong et al., "β-Glucan Functions as an Adjuvant for Monoclonal Antibody Immunotherapy by Recruiting Tumoricidal Granulocytes as Killer Cells", *Cancer Res.*, Dec. 15, 2003; 63(24):9023-31.

Hong et al., "Mechanism by Which Orally Administered β-1,3-Glucans Enhance the Tumoricidal Activity of Antitumor Monoclonal Antibodies in Murine Tumor Models", *J Immunol.*, Jul. 15, 2004; 173(2):797-806.

Howard, "Methylamine Reaction and Denaturation-dependent Fragmentation of Complement Component 3: Comparison with $\alpha_2$-Macroglobulin", *J Biol Chem.*, Aug. 10, 1980; 255(15):7082-7084.

Kennedy et al., "Dectin-1 promotes fungicidal activity of human neutrophils", *Eur J Immunol.*, Feb. 2007; 37(2):467-478.

Kilgore et al., "Neutrophils and reactive oxygen intermediates mediate glucan-induced pulmonary granuloma formation through the local induction of monocyte chemoattractant protein-1", *Lab Invest.*, Feb. 1997; 76(2):191-201.

Lavigne et al., "β-Glucan Is a Fungal Determinant for Adhesion-Dependent Human Neutrophil Functions", *J Immunol.*, Dec. 15, 2006; 177(12):8667-8675.

Law et al., "Covalent binding and hemolytic activity of complement proteins", *Proc Natl Acad Sci U S A.*, Dec. 1980; 77(12):7194-7198.

Lepow et al., "Chromatographic resolution of the first component of human complement into three activities", *J Exp Med.*, Jun. 1, 1963; 117:983-1008.

Li et al., "Yeast β-Glucan Amplifies Phagocyte Killing of iC3b-Opsonized Tumor Cells via Complement receptor 3-Syk-Phosphatidylinositol 3-Kinase Pathway", *J Immunol,.* Aug. 1, 2006; 177(3):1661-1669.

Milton et al., "Enzyme-Linked Immunosorbent Assay Specific for (1-6) Branched, (1-3)-β--D--Glucan Detection in Enviormental Samples", *Appl. Environ. Microbiol.*, Dec. 2001; 67(12):5420-5424.

Palma et al., "Ligands for the β-Glucan Receptor, Dectin-1, Assigned Using "Designer" Microarrays of Oligosaccharide Probes (Neoglycolipids) Generated from Glucan Polysaccharides", *J Biol Chem,*. Mar. 3, 2006; 281(9):5771-5779.

Pillemer et al., "The Properdin System and Immunity: I. Demonstration and Isolation of a New Serum Protein, Properdin, and Its Role in Immune Phenomena", *Science*, Aug. 20, 1954; 120(3112):279-85.

Pillemer et al., "The Properdin System and Immunity: III. The Zymosan Assay of Properdin", *J Exp Med.*, Jan. 1, 1956; 103(1):1-13.

Pretus et al. "Isolation, physicochemical characterization and preclinical efficacy evaluation of soluble scleroglucan", *J. Pharm. Exp. Ther.*, Apr. 1991; 257(1):500-510 Abstract.

Ricklin et al., "Compstatin: a complement inhibitor on its way to clinical application", *Adv Exp Med Biol.*, Lambris (Ed.), *Current Topics in Complement II*, Springer Science+Business Media, LLC, 2008 632:273-292.

Rosenthal et al., "Leishmania major-human macrophage interactions: cooperation between Mac-1 (CD11b/CD18) and complement receptor type 1 (CD35) in promastigote adhesion", *Infect Immun.*, Jun. 1996; 64(6):2206-2215.

Ross et al., "Membrane complement receptor type three ($CR_3$) has lectin-like properties analogous to bovine conglutinin as functions as a receptor for zymosan and rabbit erythrocytes as well as a receptor for iC3b", *J Immunol.*, May 1985; 134(5):3307-3315.

Ross et al., "Specificity of Membrane Complement Receptor Type Three ($CR_3$) for β-Glucans", *Complement*, 1987; 4(2):61-74.

Rubin-Bejerano et al., "Phagocytosis by Human Neutrophils is Stimulated by a Unique Fungal Cell Wall Component", *Cell Host Microbe*, Jul. 12, 2007; 2(1):55-67.

Sahu et al., "Inhibition of Human Complement by a C3-Binding Peptide Isolated from a Phage-Displayed Random Peptide Library", *J Immunol.*, 1996; 157:884-891.

Sahu et al., "Structure and biology of complement protein C3, a connecting link between innate and acquired immunity", *Immunol Rev.*, Apr. 2001; 180:35-48.

Sanchez-Madrid et al., "A human leukocyte differentiation antigen family with distinct α-subunits and a common β-subunit: The lymphocyte function-associated antigen (LFA-1), the C3bi complement receptor (OKM1/Mac-1), and the p150,95 molecule", *Journal of Experimental Medicine*, Dec. 1983; 158:1785-1803.

Schenkein et al., "The role of immunoglobulins in alternative complement pathway activation by zymosan: I. Human IgG with Specificity for Zymosan Enhances Alternative Pathway Activation by Zymosan", *J Immunol.*, Jan. 1981; 126(1):7-10.

Silversmith et al., "Fluid-Phase Assembly of the Membrane Attack Complex of Complement", *Biochemistry*, Feb. 25, 1986; 25(4):841-851.

Sipka et al., "Effect of lentinan on the chemiluminescence produced by human neutrophils and the murine macrophage cell line C4Mφ", *Int J Immunopharmac*, 1985; 7(5):747-751.

Sutterwala et al., "Cooperation between CR1 (CD35) and CR3 (CD 11b/CD18) in the binding of complement-opsonized particles", *J Leukoc Biol.*, Jun. 1996; 59(6):883-890.

Taylor et al., "Dectin-1 is required for β-glucan recognition and control of fungal infection", *Nat Immunol.*, Jan. 2007; 8(1):31-38.

Thornton et al., "Analysis of the Sugar Specificity and Molecular Location of the β-Glucan-Binding Lectin Site of Complement Receptor Type 3 (CD11b/CD18)", *Journal of Immunology*, 1996; 156:1235-1246.

Ujita et al., "Carbohydrate Binding Specificity of Recombinant Human Macrophage β-Glucan Receptor Dectin-1", *Biosci Biotechnol Biochem.*, Jan. 2009; 73(1):237-240.

van Bruggen et al., "Complement receptor 3, not Dectin-1, is the major receptor on human neutrophils for β-glucan-bearing particles", *Mol Immunol.*, Dec. 2009; 47(2-3):575-578.

van Lookeren Campagne et al., "Macrophage complement receptors and pathogen clearance", *Cell Microbiol.*, Sep. 2007; 9(9):2095-2102. Epub Jun. 21, 2007.

Vetvicka et al., "Soluble β-Glucan Polysaccharide Binding to the Lectin Site of Neutrophil or Natural Killer Cell Complement Receptor Type 3 (CD11b/CD18) Generates a Primed State of the Receptor Capable of Mediating Cytotoxicity of iC3b-Opsonized Target Cells", *J Clin Invest.*, Jul. 1996; 98(1):50-61.

Vukajlovich, "Antibody-Independent Activation of the Classical Pathway of Human Serum Complement by Lipid A Is Restricted to

(56) References Cited

OTHER PUBLICATIONS

Re-Chemotype Lipopolysaccharide and Purified Lipid A", *Infect Immun*,. Sep. 1986; 53(3):480-485.
Wakshull et al., "PGG-Glucan, a soluble β-(1,3)-glucan, enhances the oxidative burst response, microbicidal activity, and activates an NF-κB-like factor in human PMN: Evidence for a glycosphingolid β-(1,3)-glucan receptor", *Immunopharmacology*, 1999; 41:89-107.
Walport, "Complement: First of Two Parts", *N Engl J Med.*, Apr. 5, 2001; 344(14):1058-1066.
Walport, "Complement: Second of Two Parts", *N Engl J Med.*, Apr. 12, 2001; 344(15):1140-4.
Willment et al., "Characterization of the Human β-Glucan Receptor and Its Alternatively Spliced Isoforms", *J Biol Chem.*, Nov. 23, 2001; 276(47):43818-43823.
Willment et al., "The human β-glucan receptor is widely expressed and functionally equivalent to murine Dectin-1 on primary cells", *Eur J Immunol.*, May 2005; 35(5):1539-1547.
Wilson et al., "Contribution of Antibody in Normal Human Serum to Early Deposition of C3 onto Encapsulated and Nonencapsulated *Cryptococcus neoformans*", *Infect Immun*, 1992; 60(3):754-761.
Xia et al., "Generation of Recombinant Fragments of CD11b Expressing the Functional β-Glucan-Binding Lectin Site of CR3 (CD11b/CD18)", *Journal of Immunology*, Jun. 15, 1999; 162:7285-7293.
Xia et al., "The β-Glucan-Binding Lectin Site of Mouse CR3 (CD11b/CD18) and Its Function in Generating a Primed State of the Receptor That Mediates Cytotoxic Activation in Response to iC3b-Opsonized Target Cells", *J Immunol*, Feb. 15, 1999; 162(4):2281-2290.
Xiong et al., "Modulation of CD11b/CD18 Adhesive Activity by Its Extracellular, Membrane-Proximal Regions", *J Immunol.*, Jul. 15, 2003; 171(2):1042-1050.
Yan et al., "Critical role of Kupffer cell CR3 (CD11b/CD18) in the clearance of IgM-opsonized erythrocytes or soluble β-glucan", *Immunopharmacology*, 2000; 46(1):39-54.
Zhang et al., "Activation, Binding, and Processing of Complement Component 3 (C3) by *Blastomyces dermatitidis*", *Infect. Immun.*, May 1997; 65(5):1849-1855.
Zhang et al., "Role of Glucan and Surface Protein BAD1 in Complement Activation by *Blastomyces dermatitidis* Yeast", *Infect. Immun.*, Dec. 2001; 69(12):7559-7564.
Lowman et al. "Structural characterization of (10 3)-b-D-glucans isolated from blastospore and hyphal forms of Candida albicans", 2003, *Carbohydrate Research* 338:1491-1496.
Akramienė et al., "Effects of β-glucans on the immune system," *Medicina (Kaunas)*, 2007;43(8):597-606.
Davis et al., "Effects of Oat β-Glucan on Innate Immunity and Infection after Exercise Stress," *Med Sci Sports Exercise*, Aug. 2004;36(8):1321-1327.
Bose, et al., "Binding of soluble yeast β-glucan to human neutrophils and monocytes is complement-dependent", Aug. 12, 2013, *Frontiers in Immunology: Molecular Innate Immunity*, vol. 4, Article 230, pp. 1-14.

\* cited by examiner

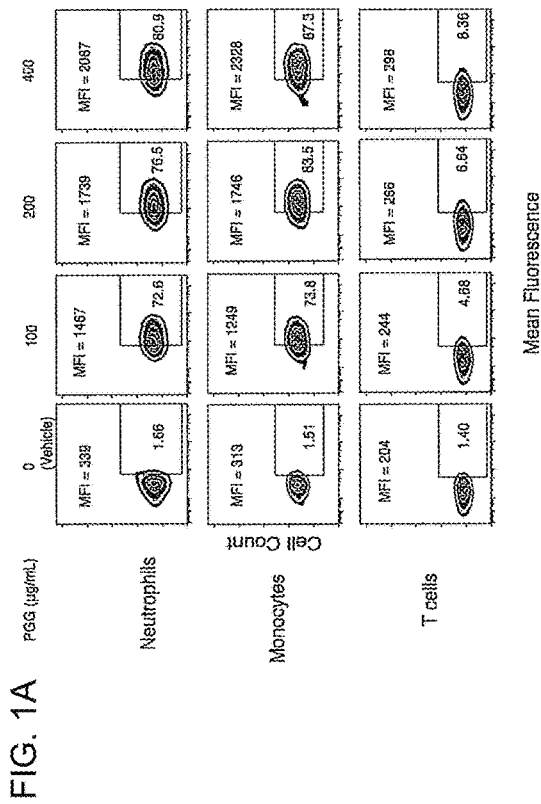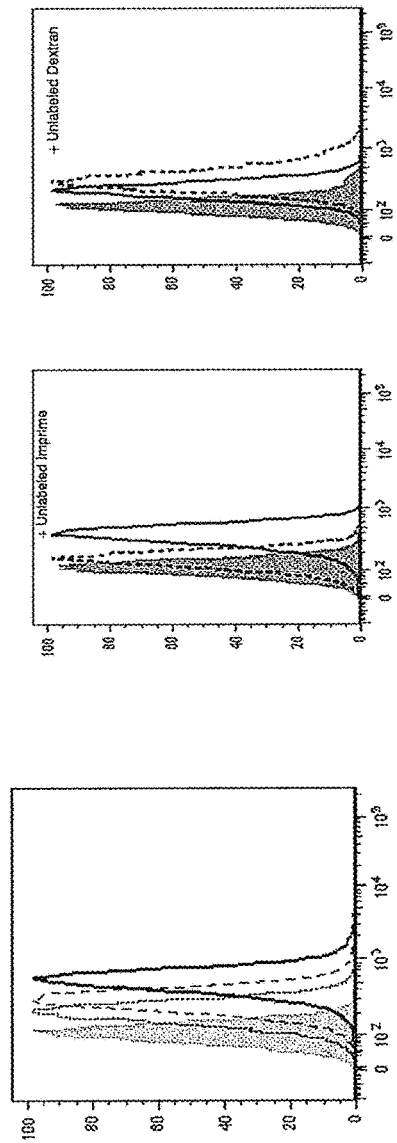
FIG. 1A
FIG. 1B
FIG. 1C

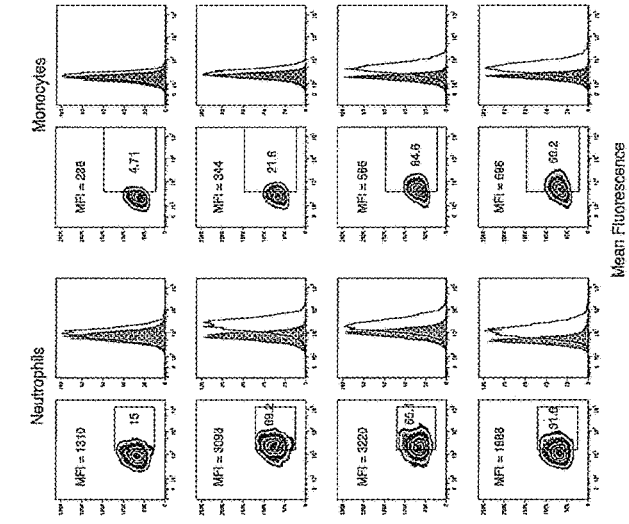
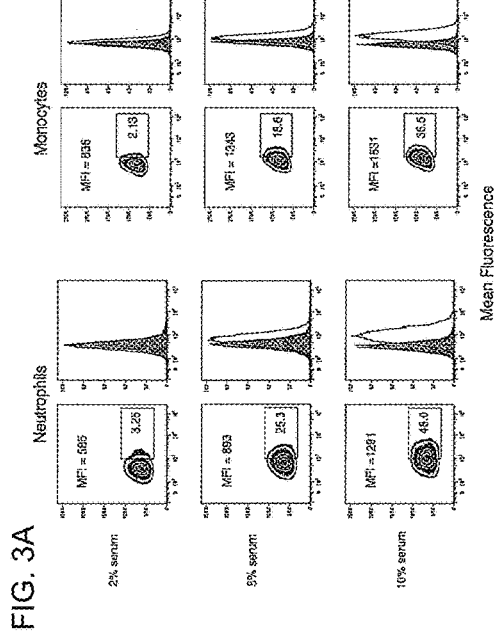
FIG. 3A
FIG. 3B
FIG. 3C

ОPSONIZED β-GLUCAN PREPARATIONS AND METHODS

CROSS-REFERENCE TO RELATED APPLICATION

This application is a § 371 U.S. National Stage of International Application No. PCT/US2012/040435, filed Jun. 1, 2012, which claims priority to U.S. Provisional Patent Application Ser. No. 61/493,101, filed Jun. 3, 2011, each of which is incorporated by reference herein in its entirety.

BACKGROUND

β-glucans are polymers of glucose derived from a variety of microbiological and plant sources including, for example, yeast, bacteria, algae, seaweed, mushroom, oats, and barley. Of these, yeast β-glucans have been extensively evaluated for their immunomodulatory properties. Yeast β-glucans are represented in various forms such as intact yeast, zymosan, purified whole glucan particles, solubilized zymosan polysaccharide, or highly-purified soluble β-glucans of different molecular weights (1-11). Structurally, yeast β-glucans are composed of glucose monomers organized as a β-(1,3)-linked glucopyranose backbone with periodic β-(1,3) glucopyranose branches linked to the backbone via β-(1,6) glycosidic linkages. The different forms of yeast β-glucans can function differently from one another. The mechanism through which yeast β-glucans exert their immunomodulatory effects can be influenced by the structural differences between different fauns of the β-glucans such as, for example, its particulate or soluble nature, tertiary conformation, length of the main chain, length of the side chain, and frequency of the side chains. The immune stimulating functions of yeast β-glucans are also dependent upon the receptors engaged in different cell types in different species, which again, is dependent on the structural properties of the β-glucans.

Complement proteins in the serum, specifically C3 and C1q, are serum pattern recognition receptors (PRRs) that recognize pathogens and are subsequently activated by the classical, alternative, or lectin pathways (Brown G D 2006). All three share the initial step of C3 activation and breakdown into C3a and C3b proteins, and the final step of forming the cytolytic membrane attack complex (MAC) consisting of complement proteins C5b, C6, C7, C8, and C9 (C5b-9). After the initial break down of C3, C3b covalently associates with the carbohydrates or proteins present on the surface of pathogens. This initial process of C3b attachment to the pathogens is followed by further breakdown of bound C3b into iC3b, C3c, and C3dg fragments which ultimately lead to complete opsonizing of the pathogen (Reviewed in Walport 2001). Complement opsonizing of pathogens can lead to either direct killing of the pathogen by forming the MAC or to indirect recognition and destruction of the pathogen by opsonic receptors such as complement receptors on the leucocytes. Zymosan, a crude particulate β-glucan obtained from cell walls of *Saccharomyces cerevisiae* has been well known for years as the stimulator of the antibody independent alternative pathway of complement activation (Czop J K 1985, Fearon D T 1977, Pillemer 1954, Pillemer 1956).

SUMMARY

In one aspect, the invention provides a composition that generally includes isolated opsonized soluble β-glucan. In some embodiments, the soluble β-glucan may be derived from yeast such as, for example, *Saccharomyces cerevisiae*. In some embodiments, the soluble β-glucan can include β(1,6)-[poly-1,3)-D-glucopyranosyl]-poly-b(1,3)-D-glucopyranose. In some embodiments, the opsonized soluble β-glucan can include an opsonin coupled to the β-glucan. In some embodiments, the opsonin can include C3, C3a, C3b, iC3b, C3bB, C3bBb, C3d, C3dg, C4, C5, C5a, C5b, C6, C7, C8, C9, or any combination of two or more thereof.

In some embodiments, the composition can further include an active agent coupled to the opsonized soluble β-glucan.

In some embodiments, the composition can further include serum.

In another aspect, the invention provides a method that generally includes contacting soluble β-glucan with a composition under conditions effective for at least one component of the composition to opsonize the soluble β-glucan, thereby forming an opsonization mixture, wherein the composition comprises sufficient components of the complement system to opsonize the soluble β-glucan. In some embodiments, the composition with which the soluble β-glucan is contacted can include serum. In some embodiments, the conditions can include incubating the composition and soluble β-glucan together at a temperature of from about 25° C. to about 45° C. In some embodiments, the conditions can include incubating the composition and soluble β-glucan together for at least 15 minutes. In some embodiments, the conditions can include providing no more than 1.25 µg of β-glucan per 1 µL of composition such as, for example, providing at least a 10-fold volume excess of the composition compared to the volume of β-glucan. In some embodiments, the method can further include isolating at least a portion of the opsonized soluble β-glucan from the opsonization mixture.

In another aspect, the invention provides a method that generally includes administering opsonized soluble β-glucan to a individual in an amount effective to increase at least one of the following compared to non-opsonized β-glucan: binding of the opsonized soluble β-glucan to B cells, monocytes, or neutrophils; migration of neutrophils toward the opsonized soluble β-glucan; and the individual's immunomodulatory function. In some embodiments, the opsonized soluble β-glucan can include an active agent coupled to the opsonized soluble β-glucan. In some embodiments, the soluble β-glucan is derived from yeast such as, for example, *Saccharomyces cerevisiae*. In some embodiments, the soluble β-glucan can include β(1,6)-[poly-1,3)-D-glucopyranosyl]-poly-b(1,3)-D-glucopyranose.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 1. Concentration-dependent binding of PGG β-glucan to human neutrophils and monocytes Binding of PGG β-glucan at various concentrations to isolated human neutrophils, monocytes and T-cells identified within PBMC population was measured as described in Material and Methods. A) Bound PGG β-glucan after incubation with the cells (1×10⁶ cells/mL) in complete media (RPMI+10% autologous serum) at concentrations 100 μg/mL, 200 μg/mL, or 400 μg/mL at 37° C. for two hours was detected by staining with β-glucan-specific mouse monoclonal antibody BfD IV as the primary antibody and FITC-labeled goat anti-mouse IgM as the secondary antibody. The mean fluorescence intensity (MFI) and percentage of the β-glucan-treated, BfD IV positive neutrophils, monocytes, and T-cells in comparison to those of the vehicle treated group are stated in the zebra plots. B) Concentration dependent DTAF staining observed on neutrophils incubated for one hour at 37° C. with 25 βg/mL (dotted), 100 μg/mL (dashed), or 400 μg/mL (solid) DTAF-labeled β-glucan in comparison to that of the vehicle (gray filled) treated control group. C) Neutrophils in complete media were incubated with 10 mg/mL of unlabeled PGG β-glucan or dextran for 30 minutes at 37° C. before incubation with 25 μg/mL DTAF-labeled β-glucan for 30 minutes at 37° C. The histogram shows DTAF staining of DTAF-labeled β-glucan treated neutrophils in the presence (dotted) or absence (solid) of excess unlabeled β-glucan or dextran in comparison to that of the vehicle treated neutrophils (gray filled). Data shown here is representative of at least three experiments performed with cells obtained from three different donors.

FIG. 3. Time, temperature, and serum dependent binding of PGG β-glucan to human neutrophils and monocytes Optimal conditions for binding of 200 μg/mL and 100 μg/mL PGG β-glucan to neutrophils, and monocytes within PBMC (1×10⁶ cells/mL) were investigated as described in Materials and Methods. A) The influence of serum was studied by measuring binding of β-glucan to neutrophils and monocytes within PBMC in media containing 2%, 5%, or 10% autologous serum. B) In the time course study, binding was measured after incubating the β-glucan with neutrophils and PBMC in complete media at 37° C. for 10 minutes, 30 minutes, 60 minutes, or 120 minutes. For the temperature study, binding was measured after the cells were incubated with the β-glucan for 2 hours at either 4° C., room temperature, or 37° C. The zebra plots showing the MFI and percentage of BfD IV positive cells, and the histograms showing the fluorescence intensity of cells treated with β-glucan (solid) in comparison to that of the vehicle (gray filled) treated control group indicate that optimal binding of β-glucan to both monocytes and neutrophils required the presence of 10% autologous serum in the media, an incubation period of 1-2 hours, and an incubation temperature of 37° C. with the cells. Data shown here is representative of three experiments performed with cells obtained from three different donors.

DETAILED DESCRIPTION OF ILLUSTRATIVE EMBODIMENTS

Figure 2:
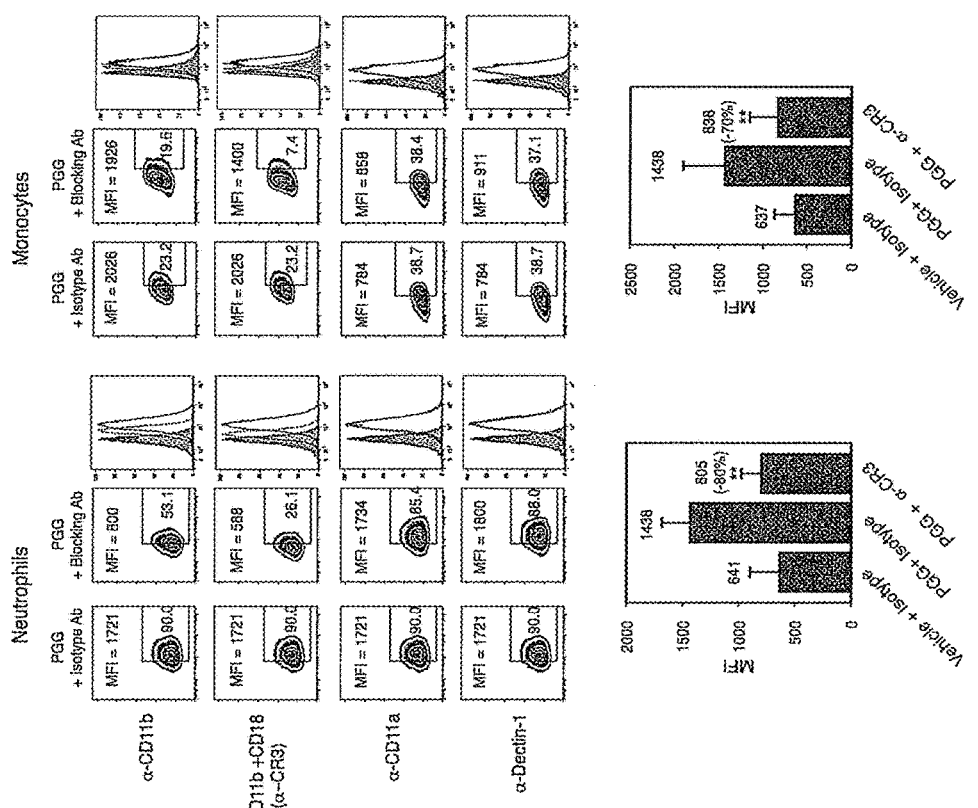
FIG. 2. Role of CR3 receptor in binding of PGG β-glucan to human neutrophils and monocytes Binding of 200 μg/mL PGG β-glucan to isolated human neutrophils and 100 μg/mL to monocytes within PBMC was measured with or without CR3 or Dectin-1 receptor blocking antibodies as described in Material and Methods. A) Binding was measured after blocking only the CD11b chain of CR3 receptor (LM2/1: 10 μg/10⁶ cells) and VIM12: 10 μg/10⁶ cells), or CD11a chain of an irrelevant integrin, LFA-1 receptor (HI11: 10 μg/10⁶ cells), or both CD11b and CD18 chains of CR3 (LM2/1 and VIM12 and IB4: 10 μg of each/10⁶ cells), or Dectin-1 receptor (GE2: 10 μg/10⁶ cells). The cells were pre-incubated for 30 minutes on ice with the different blocking antibodies or equal concentration of relevant isotype controls before adding β-glucan. The MFI and percentage of β-glucan-treated, BfD IV positive cells in the presence of isotype control or blocking antibodies are stated in the zebra plots. The histogram shows β-glucan binding in the presence of isotype controls (solid) and blocking antibodies (dotted) is compared to vehicle control (grey filled). The binding inhibition was very effective when CR3 was blocked using the combination of antibodies to both CD11b and CD18 chains. Data shown is representative of three independent experiments performed in three different donors. The graphical representation of mean MFI±SEM of vehicle treated control group, β-glucan treated group in the presence of CR3 blocking or isotype control antibodies from five donors show that binding in the presence of anti-CR3 antibodies was significantly lower than that in the presence of isotype control antibodies. The average MFI and percentage of inhibition calculated by the formula described in Material and Methods (in parentheses) are stated on the graph. **, p<0.05 compared to β-glucan-treated group in the presence of isotype controls.

Imprime PGG (β(1,6)-[poly-1,3)-D-glucopyranosyl]-poly-β(1,3)-D-glucopyranose) is a highly purified and well characterized soluble form of yeast-derived β-glucan. We recently investigated the ability of Imprime PGG to be opsonized by complement proteins in serum. We also investigated the functional consequence of opsonizing Imprime PGG such as, for example, binding to human immune cells. This is the first time a soluble yeast glucan has been shown to be complement opsonized before binding to a complement receptor.

Thus, in one aspect, the invention provides a composition that generally includes isolated opsonized soluble β-glucan. In some cases, the opsonized soluble β-glucan may be prepared by in vitro incubation of the soluble β-glucan with sufficient components of the complement system to result in opsonization of the soluble β-glucan. In other cases, the opsonized soluble β-glucan may be prepared by covalently derivatizing the soluble β-glucan with one or more complement proteins or complement-like proteins to mimic the natural β-glucan/complement complex that may be formed when the soluble β-glucan is contacted with serum, whether in vivo or when incubated in vitro.

Opsonized soluble β-glucan may exhibit enhanced binding to human immune cells compared to unopsonized soluble β-glucan. In vitro, unopsonized β-glucan can bind poorly to human immune cells such as, for example, B cells, monocytes, and neutrophils. When administered to a subject, soluble β-glucan may become opsonized. Indeed, we show that the binding of opsonized soluble β-glucan to B-cells, monocytes, and neutrophils is enhanced significantly with increasing concentrations of serum. Pre-opsonized soluble β-glucan, when added to cells in heat-inactivated serum (e.g., non-permissive binding conditions), completely rescues binding on all three cell types. Thus, opsonized soluble β-glucan can be administered to a subject and provide more rapid immunomodulatory β-glucan activity than administering unopsonized soluble β-glucan because (a) the pre-opsonized soluble β-glucan can more readily bind and affect cells of the immune system compared to unopsonized soluble β-glucan, and (b) the pre-opsonized soluble β-glucan does not require opsonizing in vivo in order to exhibit the opsonized immunomodulatory activity. The opsonized soluble β-glucan also can be administered to subjects with deficient opsonic activities of the complement system (e.g., pyogenic bacterial infections and membranoproliferative glomerulonephritis).

Opsonized soluble β-glucan also can act as a chemoattractant stimulus for innate human immune cells such as, for example, neutrophils. We show enhanced migration of neutrophils to pre-opsonized soluble β-glucan compared to neutrophil migration toward unopsonized soluble β-glucan. Here again, administering an opsonized soluble β-glucan to a subject can provide the chemoattractant stimulus more rapidly than by administering unopsonized soluble β-glucan.

Opsonized soluble β-glucan also may be able to engage complement receptors on human immune cells including, for example, the CR2 receptor on B-cells and the CR3 receptor on monocytes and neutrophils. By binding to complement receptors on the human immune cells, opsonized soluble β-glucan can elicit various immunomodulatory functions such as, for example, B cell proliferation, neutrophil migration, etc.

As used herein, the term "isolated" and variations thereof refer to opsonized soluble β-glucan that has been removed, to any degree, from its naturally-occurring environment. For instance, isolated opsonized soluble β-glucan includes opsonized soluble β-glucan that has been removed from serum so that, for example, at least a portion of the proteins native to the serum are no longer present. The term "isolated" does not convey any specific degree to which the other cellular components are removed.

"Opsonized" and variations thereof refer to soluble β-glucan molecules that include at least one opsonin. An "opsonin" refers to, for example, a complement-associated protein or fragment thereof including, for example, C3, C3a, C3b, iC3b, C3bB, C3bBb, C3d, C3dg, C4, C5, C5a, C5b, C6, C7, C8, C9, or any combination of two or more thereof. In some embodiments, the opsonin may be coupled directly or indirectly to the soluble β-glucan. The β-glucan and the opsonin may be covalently coupled or, in some embodiments, may include at least one affinity or ionic bond. As used herein, "covalently coupled" refers to direct or indirect coupling of two components exclusively through covalent bonds. Direct covalent coupling may involve direct covalent binding between an atom of the β-glucan and an atom of the opsonin. Alternatively, the covalent coupling may occur through a linking group covalently attached to the β-glucan moiety, the opsonin, or both, that facilitates covalent coupling of the β-glucan and the opsonin. Indirect covalent coupling may include a third component such as, for example, a solid support to which the β-glucan and the opsonin are separately covalently attached.

When present, the linking group can be any suitable organic linking group that allows the β-glucan to be covalently coupled to the opsonin while preserving at least a portion of the immunomodulatory activity of the β-glucan/opsonin complex. The linking group can include a reactive group capable of reacting with the opsonin to form a covalent bond. Suitable reactive groups include, for example, those discussed in Hermanson, G. (1996), *Bioconjugate Techniques*, Academic Press, Chapter 2 "The Chemistry of Reactive Functional Groups", 137-166. For example, the linking group may react with a primary amine (e.g., an N-hydroxysuccinimidyl ester or an N-hydroxysulfosuccinimidyl ester); it may react with a sulfhydryl group (e.g., a maleimide or an iodoacetyl), or it may be a photoreactive group (e.g. a phenyl azide including 4-azidophenyl, 2-hydroxy-4-azidophenyl, 2-nitro-4-azidophenyl, and 2-nitro-3-azidophenyl).

A chemically active group accessible for covalent coupling to the linking group can include a group that may be used directly for covalent coupling to the linking group or, alternatively, a group that may be modified to be available for covalent coupling to the linking group. For example, suitable chemically active groups include but are not limited to primary amines and sulfliydryl groups. Because certain active moieties—e.g., proteins and other peptides—may include a plurality of chemically active groups, it is possible that an opsonized soluble β-glucan can include a plurality of soluble β-glucan molecules coupled to an opsonin, a plurality of opsonins coupled to a soluble β-glucan, or a plurality of opsonins and a plurality of β-glucans.

Certain opsonized soluble β-glucans may contain chemical associations between a β-glucan and an opsonin other than covalent coupling. The chemical association need only be strong enough to maintain the coupling of the opsonin and the β-glucan for its intended use such as, for example, administration to a subject, delivery to a targeted tissue or organ, or for performing an assay (e.g., a detection assay). Thus, a wide variety of non-covalent couplings are possible and may be identified as suitable depending upon the conditions to which the opsonized soluble β-glucan will be exposed such as, for example, pH, temperature, the duration of coupling required for the intended use, etc. For example, an opsonized soluble β-glucan may include an affinity interaction between the β-glucan and the opsonin. Avidin-biotin affinity represents one example of a non-covalent interaction that may be utilized to couple an opsonin and a β-glucan. For example, a biotin molecule may be covalently attached to an opsonin via one of a number of functional groups present on amino acids (e.g., primary amines or sulthydryl groups), a β-glucan may be coupled to an avidin molecule by appropriate derivatization of the β-glucan, and the opsonin and β-glucan may be non-covalently coupled to one another through the avidin-biotin affinity interaction. Methods for biotinylating proteins and linking chemical groups to avidin are well known to one of skill in the art. Alternative affinity interactions that may be useful for making β-glucan compounds include, for example, antigen/antibody interactions and glycoprotein/lectin interactions.

The soluble β-glucan may be any form of β-glucan that is soluble in water. Suitable soluble β-glucans and the preparation of suitable soluble β-glucans from their natural sources are described in, for example, U.S. Patent Application Publication No. US2008/0103112 A1. In some embodiments, the soluble β-glucan may be derived from yeast such as, for example, Saccharomyces cerevisiae. In certain specific embodiments, the soluble β-glucan may be, or be derived from β(1,6)-[poly-1,3)-D-glucopyranosyl]-poly-β(1,3)-D-glucopyranose, also referred to herein as PGG. Thus, the soluble β-glucan can include, for example, modified and/or derivatized soluble β-glucans such as those described in International Patent Application No. PCT/US12/36795. In other embodiments, the soluble β-glucan can include, for example, a particulate-soluble β-glucan or a particulate-soluble β-glucan preparation, each of which is described in, for example, U.S. Pat. No. 7,981,447.

Thus, in another aspect, the invention provides a method of producing opsonized soluble β-glucan. Generally, the method includes contacting soluble β-glucan with a composition under conditions effective for at least one component of the composition to opsonize the soluble β-glucan. The composition generally includes sufficient components of the complement system to opsonize the soluble β-glucan. In some embodiments, the composition with which the soluble β-glucan is contacted can include a blood product such as, for example, serum. As used herein, "blood product" refers to whole blood or portion thereof (e.g., serum) with sufficient components of complement system to opsonize a target of opsonization such as, for example, an antigen or a soluble β-glucan.

In some embodiments, the conditions can include incubating the composition and soluble β-glucan together at a temperature of from about 25° C. to about 45° C., although it is feasible that the method may be performed by incubating the composition and β-glucan at a temperature outside of this range. Thus, in some embodiments, the composition and β-glucan may be incubated at a minimum temperature of, for example, at least 25° C., at least 27° C., at least 30° C., at least 35° C., at least 37° C., or at least 40° C. In some embodiments, the composition and β-glucan may be incubated at a maximum temperature of, for example, no more than 45° C., no more than 40° C., no more than 37° C., no more than 35° C., or no more than 30° C. In some embodiments, the temperature at which the composition and β-glucan may be incubated can fall within a range having endpoints defined by any minimum temperature and any appropriate maximum temperature described herein. In one particular embodiment, the composition and β-glucan may be incubated at a temperature of 37° C.

In some embodiments, the conditions can include incubating the composition and β-glucan together for a period of from about 15 minutes to about 120 minutes, although it is feasible that the method may be performed by incubating the composition and β-glucan together for a period outside of this range. Thus, the composition and β-glucan may be incubated together for a minimum of at least 15 minutes such as, for example, at least 20 minutes, at least 30 minutes, at least 45 minutes, at least 60 minutes, at least 75 minutes, or at least 90 minutes. In some embodiments, the composition and β-glucan may be incubated together for a maximum of no more than 120 minutes such as, for example, no more than 75 minutes, no more than 60 minutes, or no more than 45 minutes. In some embodiments, the length of time that the composition and β-glucan are incubated together may fall within a range having endpoints defined by any minimum length of time and any appropriate maximum length of time. In one particular embodiment, the composition and β-glucan may be incubated together for about 30 minutes.

In some embodiments, the conditions can include providing the composition and β-glucan in a specified ratio such as, for example, providing no more 1.25 μg of β-glucan per 1 μL, of composition. In some embodiments, the conditions include providing a volume:mass (e.g., μL:μg) excess of the composition compared to the amount of β-glucan such as, for example, at least a two-fold excess (e.g., 2 μL, composition per 1 μg of β-glucan), at least a three-fold excess, at least a four-fold excess, at least a five-fold excess, at least a six-fold excess, at least a seven-fold excess, at least an eight-fold excess, at least a nine-fold excess, at least a 10-fold excess, at least a 15-fold excess, at least a 20-fold excess, or at least a 25-fold excess of composition compared to the amount of β-glucan. Thus, in one particular embodiment, the conditions include providing at least a 10-fold volume:mass excess of the composition compared to the amount of β-glucan.

In some embodiments, the method can further include isolating at least a portion of the opsonized soluble β-glucan from the opsonization mixture. The opsonized soluble β-glucan may be isolated using any suitable method for separating components of a biological or chemical mixture such as, for example, capturing opsonized β-glucan-serum using an appropriate affinity resin coupled to a monoclonal antibody to β-glucan. Suitable isolation strategies can include, for example, affinity chromatography using one or more carbohydrate binding proteins as a ligand, affinity chromatography using one or more monoclonal antibodies that specifically bind β-glucan as a ligand, or affinity chromatography using one or more monoclonal antibodies that specifically bind to one or more complement proteins. The isolated opsonized soluble β-glucan may then be formulated for administration to an individual.

The isolated opsonized soluble β-glucan may be formulated in a composition along with a "carrier." As used herein, "carrier" includes any solvent, dispersion medium, vehicle, coating, diluent, antibacterial, and/or antifungal agent, isotonic agent, absorption delaying agent, buffer, carrier solution, suspension, colloid, and the like. The use of such media and/or agents for pharmaceutical active substances is well known in the art. Except insofar as any conventional media or agent is incompatible with the isolated opsonized soluble β-glucan, its use in the therapeutic compositions is contemplated. Supplementary active ingredients also can be incorporated into the compositions.

By "pharmaceutically acceptable" is meant a material that is not biologically or otherwise undesirable, i.e., the material may be administered to an individual along with isolated opsonized soluble β-glucan without causing any undesirable biological effects or interacting in a deleterious manner with any of the other components of the pharmaceutical composition in which it is contained.

Isolated opsonized soluble β-glucan may be formulated into a pharmaceutical composition. The pharmaceutical composition may be formulated in a variety of forms adapted to a preferred route of administration. Thus, a composition can be administered via known routes including, for example, oral, parenteral (e.g., intradermal, transcutaneous, subcutaneous, intramuscular, intravenous, intraperitoneal, etc.), or topical (e.g., intranasal, intrapulmonary, intramammary, intravaginal, intrauterine, intradermal, transcutaneous, rectally, etc.). It is foreseen that a composition can be administered to a mucosal surface, such as by administration to, for example, the nasal or respiratory mucosa (e.g., by spray or aerosol). A composition also can be administered via a sustained or delayed release.

A formulation may be conveniently presented in unit dosage form and may be prepared by methods well known in the art of pharmacy. Methods of preparing a composition with a pharmaceutically acceptable carrier include the step of bringing the isolated opsonized soluble β-glucan into association with a carrier that constitutes one or more accessory ingredients. In general, a formulation may be prepared by uniformly and/or intimately bringing the active compound into association with a liquid carrier, a finely divided solid carrier, or both, and then, if necessary, shaping the product into the desired formulations.

Isolated opsonized soluble β-glucan may be provided in any suitable fowl. including but not limited to a solution, a suspension, an emulsion, a spray, an aerosol, or any form of mixture. The composition may be delivered in formulation with any pharmaceutically acceptable excipient, carrier, or vehicle. For example, the formulation may be delivered in a conventional topical dosage Rhin such as, for example, a cream, an ointment, an aerosol formulation, a non-aerosol spray, a gel, a lotion, and the like. The formulation may further include one or more additives including such as, for example, an adjuvant, a skin penetration enhancer, a colorant, a fragrance, a flavoring, a moisturizer, a thickener, and the like.

In another aspect, the invention provides methods that generally involve administering to an individual an effective amount of opsonized soluble β-glucan. As used herein, "an effective amount" refers to the amount of isolated opsonized soluble β-glucan effective to increase at least one of the following: binding of the isolated opsonized soluble β-glucan to B cells, monocytes, or neutrophils; migration of neutrophils toward the opsonized soluble β-glucan; and the individual's immunomodulatory functions including, for example, phagocytosis, oxidative burst, production of cytokines and/or chemokines, and/or initiating an adaptive immune response.

The amount of the isolated opsonized soluble β-glucan effective to induce one or more of the desired effects can, therefore vary depending on various factors including, but not limited to, the weight, physical condition, and/or age of the subject, and/or the route of administration. Thus, the absolute weight of the isolated opsonized soluble β-glucan included in a given unit dosage form can vary widely, and depends upon factors such as the species, age, weight and physical condition of the subject, as well as the method of administration. Accordingly, it is not practical to set forth generally the amount that constitutes an amount of the isolated opsonized soluble β-glucan effective for all possible applications. Those of ordinary skill in the art, however, can readily determine the appropriate amount with due consideration of such factors.

In some embodiments, the method can include administering sufficient isolated opsonized soluble β-glucan to provide a dose of, for example, from about 100 ng/kg to about 50 mg/kg to the subject, although in some embodiments the methods may be performed by administering the isolated opsonized soluble β-glucan in a dose outside this range. In some embodiments, the method includes administering sufficient the isolated opsonized soluble β-glucan to provide a dose of from about 10 µg/kg to about 5 mg/kg to the subject, for example, a dose of from about 100 µg/kg to about 1 mg/kg.

Alternatively, the dose may be calculated using actual body weight obtained just prior to the beginning of a treatment course. For the dosages calculated in this way, body surface area ($m^2$) is calculated prior to the beginning of the treatment course using the Dubois method: $m^2 = (wt\ kg^{0.425} \times height\ cm^{0.725}) \times 0.007184$. In some embodiments, therefore, the method can include administering sufficient isolated opsonized soluble β-glucan to provide a dose of, for example, from about 0.01 mg/m$^2$ to about 10 mg/m$^2$.

In some embodiments, the isolated opsonized soluble β-glucan may be administered, for example, from a single dose to multiple doses per week, although in some embodiments the method may be performed by administering the isolated opsonized soluble β-glucan at a frequency outside this range. In certain embodiments, the isolated opsonized soluble β-glucan may be administered from about once per month to about five times per week.

In some embodiments, the opsonized soluble β-glucan may be coupled to an active agent. A soluble β-glucan and an active agent may be coupled by, for example, any of the covalent coupling methods and/or non-covalent chemical associations described above with respect to embodiments in which the β-glucan and opsonin are coupled. Generally, an active agent may be an agent that can enhance opsonization, targeted delivery, and/or activity of an opsonized soluble β-glucan. In other cases, an active agent can include agents whose activity is enhanced by opsonized soluble β-glucan.

Certain antibodies can enhance opsonization of a soluble β-glucan to which they are coupled. Thus, in some embodiments, the active agent can include one or more such antibodies coupled to the soluble β-glucan. Exemplary antibodies that can enhance opsonization include, for example, endogenous or naturally-occurring anti-glucan (e.g., anti-β-glucan) antibodies. Other exemplary antibodies that can enhance opsonization include, for example, BfD I, BfD II, BfD III, and/or BfD IV, each of which is described in U.S. Pat. No. 6,294,321.

Chemokines such as, for example, IL-8, C5a, and MCP-1 (monocyte chemoattractant protein-1) may help target a coupled opsonized soluble β-glucan to immune cells such as, for example, neutrophils and/or monocytes. Alternatively, certain antibodies (e.g., cetuximab or bevacizumab) and/or tumor-specific antigens can help target a coupled opsonized soluble β-glucan to a tumor site.

Alternatively, opsonized soluble β-glucan can exhibit enhanced binding to complement receptors on, for example, B cells. Thus, an active agent coupled to opsonized soluble β-glucan can be targeted to B cells. Exemplary active agents in this category can include, for example, an immunomodulator (e.g., agonists of Toll-like receptors (TLR agonists), certain antibodies (e.g., anti-CD40 or anti-CD137), certain antigens, a cytotoxic agent, and/or an immunosuppressive agent.

Exemplary antigens can include, for example, a viral antigen (e.g., an antigen of influenza virus, Hepatitis A, Hepatitis B, Hepatitis C, adenovirus, herpes simplex, etc.), a tumor antigen (e.g., MUC-1, CA-125, EGFR, telomerase/hTERT, PSA, MY-ESO-1, MAGE, AML1 (including AML-1 fusions), HER2/neu, gp100, WT1, CEA, etc.), a bacterial antigen (e.g., tetanus toxoid, diphtheria toxoid, *Staphylococcus* antigens, *Pneumococcus* antigens, *Klebsiella* antigens, etc.), and/or a parasitic antigen.

Exemplary cytotoxic agents can include, for example, a chemotherapeutic agent (e.g., cisplatin, cyclophosphamide, etc.), a toxin (e.g., ricin A chain, diphtheria toxin, etc.), a radioactive isotope (e.g., Yttrium-90, Iodine-131, etc.), and/or a cytokine (e.g., IL-10).

Exemplary immunosuppressive agents can include, for example, a corticosteroid, tacrolimus, methotrexate, etc.

Opsonized soluble β-glucan also may exhibit enhanced binding to complement receptors on monocytes. Thus, an active agent coupled to opsonized soluble β-glucan can be targeted to monocytes. Exemplary active agents in this category can include, for example, certain TLR agonists (e.g., agonists of TLR4, TLR7, and/or TLR8) and/or chemotherapeutic agents used to treat, for example, acute myeloid leukemia (AML, e.g., an anthracycline).

Opsonized soluble β-glucan also may exhibit enhanced binding to complement receptors located on, for example, neutrophils or red blood cells. Thus, an active agent coupled to opsonized soluble β-glucan may be targeted for delivery to neutrophils or red blood cells.

The immunomodulatory properties of yeast β-1,3/1,6 glucans are primarily mediated through their ability to be recognized by human innate immune cells. While several studies have investigated the binding of opsonized and unopsonized particulate β-glucans to human immune cells, mainly via complement receptor 3 (CR3) or Dectin-1, few have focused on understanding the binding characteristics of soluble β-glucans using a consistent, pure, and analytically-characterized source. This study evaluated the binding conditions of yeast-derived soluble β-glucan to human neutrophils and monocytes. The results demonstrated that soluble β-glucan bound to both human neutrophils and monocytes in a concentration-dependent and receptor-specific manner. Antibodies blocking the CD11b and CD18 chains of CR3 significantly inhibited binding to both the cell types, establishing CR3 as the key receptor recognizing the soluble β-glucan. Presence of serum and optimal time and temperature were shown to be the prerequisites for binding of soluble glucan. Binding inhibition in the presence of heat-inactivated serum and/or the C3-specific inhibitor, compstatin, demonstrated the involvement of complement proteins in binding. Opsonized soluble β-glucan was demonstrated by detecting iC3b, the complement opsonin on β-glucan-bound cells, as well as interaction with the β-glucan directly in both solid-phase and fluid-phase. The requirement of covalent interaction between iC3b and β-glucan was indicated by a significant reduction in the iC3b detected on β-glucan as well as binding to cells by methylamine-mediated serum inactivation. Finally, both classical and alternative pathways of complement activation are necessary for opsonizing soluble β-glucan and binding of soluble β-glucan to human immune cells.

Complement receptor 3, (CR3, CD11b/CD18, $\alpha_m\beta_2$-integrin, Mac-1) and Dectin-1 have been reported to be the predominant cell surface PRRs for particulate yeast β-glucans on innate immune cells such as, for example, monocytes, macrophages, dendritic cells, and neutrophils (1-9). CR3 is an integrin heterodimer consisting of CD11 b and CD18 subunits (Sanchez, 1983). The CD11b inserted (1)-domain binds to various ligands such as, for example, fibrinogen, ICAM-1, and iC3b, while the lectin-like domain binds to β-glucan (Ross G D, 1987; Xia Y, 1999; Vetvicka 1996; Ross G D 1985). Dectin-1 is a monomeric C-type lectin with a single extracellular C-type, β-glucan binding lectin-like domain, and a short cytoplasmic tail that contains an immunoreceptor tyrosine-based activation motif (Brown G D 2006). Early studies have shown that both complement opsonized and unopsonized particulate β-glucans bind to CR3 and Dectin-1 (Cain 1987; Ross G D 1987; Brown G D 2002; Willment 2001; Willment 2005; Ujita M 2009).

Various forms of soluble yeast-derived β-glucans have been used to demonstrate binding to CR3 and Dectin-1. Soluble zymosan polysaccharide (SZP) rich in mannan or β-glucan (~10 kDa), neutral soluble glucan, and a chemically modified soluble yeast β-glucan, 1,3 β-D-glucan phosphate (~127 kDa, glucan phosphate) have been shown to bind to CR3 on human peripheral blood isolated neutrophils (Thornton B P, 1996; Xia Y, 1999). Recombinant soluble and membrane-associated Dectin-1 was demonstrated to bind to immobilized plate-bound soluble β-glucan (24). Glucan phosphate and synthetic 1,3 β-D-glucan oligosaccharides have been shown to bind recombinant murine Dectin-1 (Adams, 2008).

No soluble yeast β-glucans have been shown to bind to a specific receptor. To add to the confusion, there are discordant results concerning the effect of any particular β-glucan on any given receptor on any given cell type. Recent studies in human neutrophils demonstrated that the major receptor for unopsonized zymosan is CR3 and not Dectin-1 (Kennedy AD 2007, van Bruggen R 2009). There is no consensus yet on the receptor for soluble glucans on human immune cells. Moreover, the soluble β-glucans used for binding studies were either minimally characterized or chemically modified. Furthermore, no studies to date have demonstrated the ability of soluble β-glucans to activate complement and the role of complement opsonization in β-glucan binding to a complement receptor.

In this study, we investigated the binding of *Saccharomyces cerevisiae*-derived, highly purified, well characterized soluble β-glucan, PGG β-glucan (m.w., approximately 120-205 kDa) to human monocytes and neutrophils, the innate immune cells that express the reported β-glucan receptors. The results demonstrate that CR3 is the main receptor for binding of the soluble β-glucan on both human neutrophils and monocytes. Moreover, we demonstrate that complement opsonizing of soluble yeast β-glucan is involved in soluble β-glucan binding to CR3.

PGG β-glucan Binds to Human Neutrophils and Monocytes in a Concentration-Dependent Manner The binding of PGG β-glucan to human neutrophils and monocytes was evaluated by incubating various concentrations of soluble β-glucan or vehicle with the cells resuspended in media with 10% autologous serum, and then staining the cells with β-glucan-specific mouse monoclonal antibody BfD IV, then fluorophore labeling with a secondary antibody. Cell surface bound β-glucan was analyzed by flow cytometry. The cells were assessed for their capacity to bind the soluble β-glucan by comparing the mean fluorescence intensity (MFI) of the cells stained with BfD IV and the percentage of cells positive for BfD IV relative to that of the vehicle treated control group. As shown in FIG. 1a, PGG β-glucan at 100 μg/mL, 200 μg/mL, and 400 μg/mL bound to both neutrophils and monocytes, but not to T-cells in a concentration-dependent manner. While the percentage of BID IV positive cells reached a plateau at 200 μg/mL, the MFI values increased with increasing concentrations of β-glucan. Binding was also assessed by the ability of DTAF-labeled PGG β-glucan to stain neutrophils and monocytes at concentrations 25 μg/mL, 100 μg/mL, and 400 μg/mL. FIG. 1b shows concentration dependent binding of DTAF-labeled β-glucan on neutrophils; the binding observed was receptor specific as the staining was blocked by excess unlabeled β-glucan, while excess of unlabeled dextran, an α-1,4/1,6 glucan did not block binding of the DTAF-labeled β-glucan to the cells (FIG. 1c).

Binding of PGG/β-glucan to Human Neutrophils and Monocytes is CR3 Dependent

In order to determine the role of CR3 or Dectin-1 in the binding of PGG β-glucan to human neutrophils and monocytes, these receptors were blocked with the receptor-specific blocking antibodies or relevant control antibodies before adding the soluble β-glucan and measurement of binding. Combinations of antibodies against either the I domain and lectin domain of the CD11b chain (LM2/1+VIM12), or against both the CD11b and CD18 chains (LM2/1+VIM12+IB4) were used to block the CR3 receptor. Dectin-1 was blocked using the GE2 antibody; the ability of GE2 to block Dectin-1-mediated function was tested by evaluating its ability to block particulate β-glucan induced oxidative burst in human peripheral blood mononuclear cells. Data presented in FIG. 2 shows that blocking the CD11b chain (LM2/1+VIM 12) partially inhibits binding of β-glucan to both neutrophils and monocytes, while blocking both the CD11b and CD18 chains (LM2/1+VIM12+IB4) further inhibits β-glucan binding. In contrast, blocking the α chain of a non-specific integrin, e.g., the CD11a chain of LFA-1, did not affect β-glucan binding. Moreover, blocking the other major β-glucan receptor, Dectin-1 (GE2), did not inhibit β-glucan binding to neutrophils or monocytes.

The average MFI of BfD IV positive cells treated with CR3 blocking antibodies (LM2/1+VIM12+IB4) from five donors was significantly lower than that of the isotype control-treated cells. Based on the MFI values, a percentage of binding inhibition by CR3 blocking antibodies was calculated relative to that of the isotype control antibodies in these five donors. The range of percentage of binding inhibition by blocking both CR3 chains in neutrophils was 69-100% with the average inhibition of 80%, while the range was 42-95% for monocytes with the average of 70%. Overall, the results demonstrate that CR3 plays a major role as a receptor involved in the binding of PGG β-glucan to human neutrophils and monocytes.

Binding of PGG β-glucan to Human Neutrophils and Monocytes is Serum, Time, and Temperature Dependent In order to determine the conditions required for PGG β-glucan binding to human neutrophils and monocytes, the influence of serum, time, and temperature were evaluated.

The role of serum in β-glucan binding to cells was evaluated after incubating cells at 37° C. for two hours in media with 2%, 5%, or 10% autologous serum. The data in FIG. 3a demonstrate that binding of soluble β-glucan, as determined by MFI and the percentage of cells labeled positive for BfD IV, increased proportionally with increase in the percentage of serum present in the media. β-glucan binding to cells required the presence of serum: minimum binding occurred using 2% serum and maximal binding occurred using 10% serum.

The kinetics of β-glucan binding were evaluated under conditions using media containing 10% serum at 37° C. Binding was measured at 10 minutes, 30 minutes, 60 minutes, and 120 minutes. The results presented in FIG. 3b demonstrate that β-glucan binding increases with incubation time. For neutrophils, maximal binding occurred at 30-60 minutes, while 60-120 minutes were required for β-glucan binding to monocytes.

The effect of temperature was evaluated by measuring binding after the cells were incubated with the soluble β-glucan for two hours at either 4° C., room temperature, or 37° C. Temperature also affected binding of β-glucan to cells: maximal binding occurred when β-glucan was incubated with cells at 37° C. as compared to 4° C. and room temperature (FIG. 3c). These data demonstrate that binding of soluble PGG β-glucan to human immune cells is serum-dependent, time-dependent, and temperature-dependent.

Binding of Soluble PGG β-glucan to Human Neutrophils and Monocytes is Dependent on Complement Proteins in the Serum After evaluating the importance of serum proteins in the binding of PGG β-glucan to immune cells, we then investigated the role that complement proteins play in binding by a) heat inactivating serum, which non-specifically inactivates complement proteins along with other heat labile proteins, and b) specifically blocking C3, the complement protein that is involved in each of the pathways—i.e., the classical, alternate, and lectin pathways—of complement activation.

Heat inactivation of serum was done by incubating the serum at 56° C. for 30 minutes. Binding in the presence of 10% human serum albumin, the most abundant serum protein, was also tested to determine whether the mere presence of a serum protein will allow for β-glucan binding to occur. For C3 blocking studies, β-glucan binding was measured in the presence of compstatin, a C3-binding synthetic peptide that inhibits all three pathways of complement activation was compared to that in the presence of a control peptide (28).

Figure 4A:
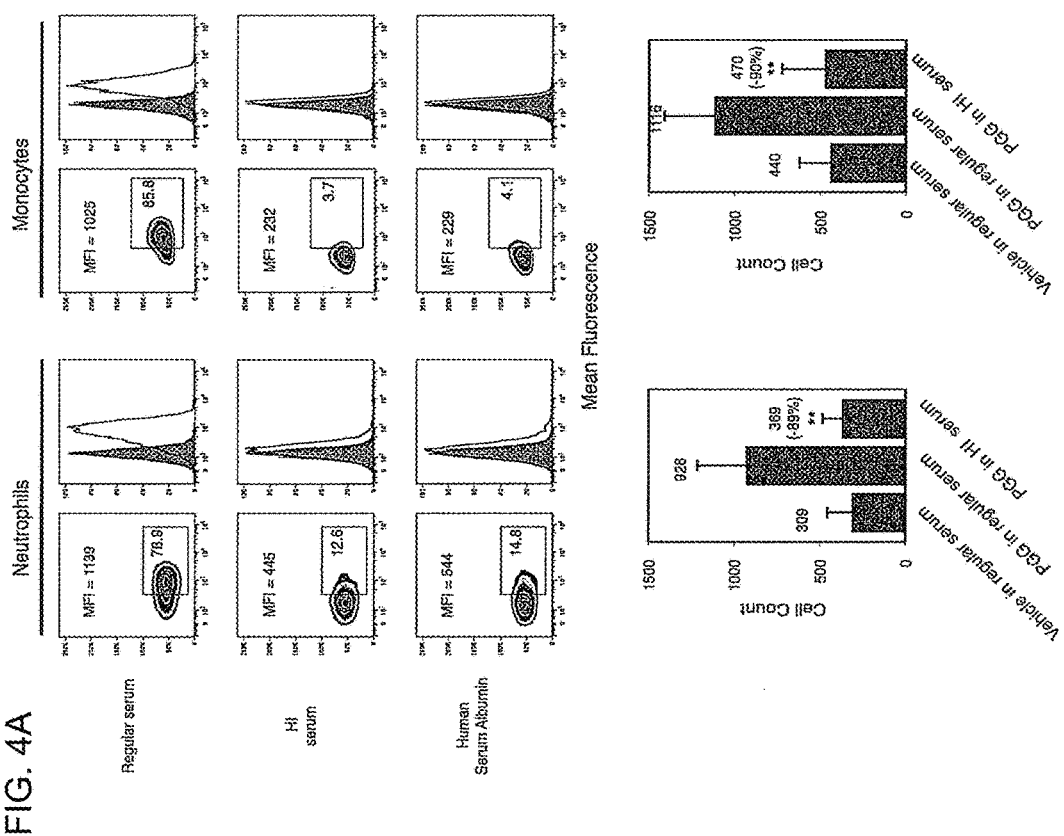
FIG. 4. Role of complement proteins in binding of PGG β-glucan to human neutrophils and monocytes The importance of complement proteins in binding of 200 μg/mL PGG β-glucan to neutrophils, and 100 μg/mL to monocytes within PBMC (1×10⁶ cells/mL) was investigated by evaluating the effects of heat inactivating the serum and specifically blocking complement protein C3 as described in the Material and Methods. A) The serum was heat inactivated (HI) by heating the serum at 56° C. for 30 minutes. Binding of β-glucan in media containing regular autologous serum was compared to that containing HI serum. Binding in the presence of 10% human serum albumin was determined to see the effect of a non-specific serum protein. The reduced MFI and percentage of BfD IV positive cells in the presence of HI serum and human serum albumin indicated diminished binding. For the various binding conditions, the histogram shows the fluorescence intensity of cells treated with β-glucan (solid) in comparison to that of the vehicle (gray filled) treated control group. Data shown in the form of zebra plots and histograms is representative of three independent experiments performed in three different donors. The average MFI of binding in the PGG β-glucan treated group in the presence of HI serum was significantly reduced in comparison to that of the group in regular serum. The MFI plot graphically represents the mean of five donors ±SEM. , p<0.05 compared to binding in regular serum. B) The serum was incubated with 20 μM compstatin, 100 μM compstatin, or peptide control for 10 minutes at room temperature and then used for binding studies. The MFI and percentage of BfD IV positive cells in the zebra plots show complete binding inhibition in the presence of 100 μM compstatin. The histogram shows the fluorescence intensity of cells treated with β-glucan in the presence of peptide control (solid) or compstatin (dotted) in comparison to that of the vehicle (gray filled) treated control group. The graphical representation of average MFI of vehicle treated control group, PGG β-glucan treated group in the presence of peptide control or 100 μM compstatin from three donors show that compstatin in comparison to peptide control significantly inhibited binding. The MFI plotted graphically represent the mean of three donors±SEM. In both the graphs, the average MFI and percentage of inhibition calculated by the formula described in Material and Methods (in parentheses) are stated on the graph , p<0.05 compared to binding in the presence of control peptide.
Figure 4B:
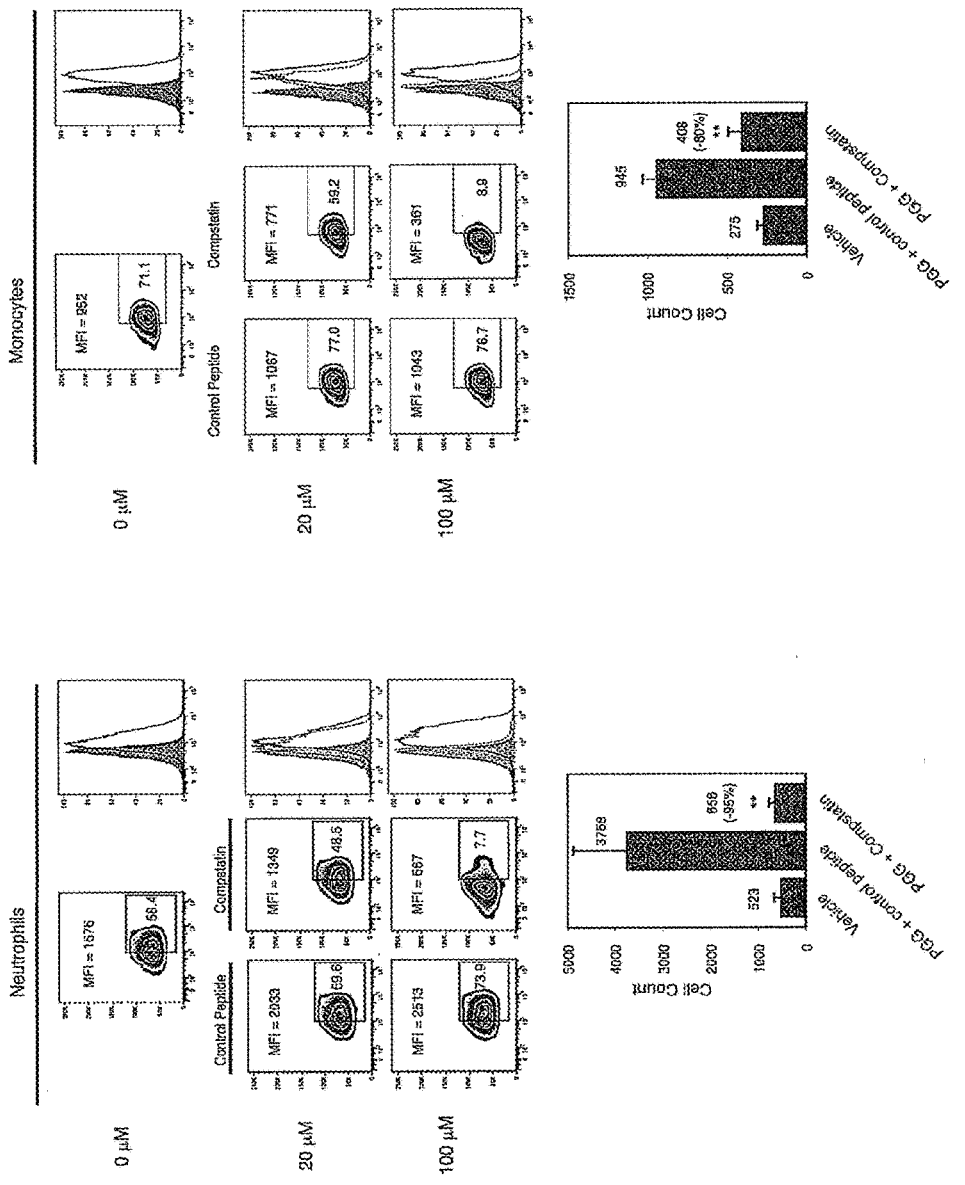

As shown in FIG. 4, binding of PGG β-glucan to neutrophils and to monocytes was abrogated in the presence of heat inactivated (HI) serum. Also, supplementing the culture media with human serum albumin (HSA) did not restore soluble β-glucan binding to cells. The statistical comparison between average MFI of glucan-bound cells in regular serum and in HI serum for five donors is shown in the graphical presentation. The percentage of binding inhibition in HI serum was calculated based on the MFI of BfD IV positive neutrophils in these five donors was 71-100% with the average inhibition being 89%, while it was 81-100% for monocytes with the average of 90%. The data in FIG. 4b further show that specifically blocking C3 using varying concentrations of compstatin inhibited binding of β-glucan in a concentration-dependent manner, with maximum inhibition observed at 100 μM. In contrast, the control peptide had no effect on binding. The average MFI of compstatin-treated neutrophils and monocytes bound to β-glucan was statistically compared to that of control peptide-treated cells in the donors: the range of percentage of inhibition was 90-98% with 95% as the average for neutrophils, and 62-92% with an average of 80% for monocytes. Taken together, these data conclusively show that complement protein, specifically C3, plays a critical role in binding of soluble PGG β-glucan to human neutrophils and monocytes.

Serum, Time, and Temperature Requirement for Binding of PGG β-glucan to Human Neutrophils and Monocytes is Primarily at the Ligand Level and not at the Receptor Level The findings of optimal serum content, and incubation time and temperature together with the critical requirement of complement protein for binding of PGG β-glucan led us to hypothesize that β-glucan is probably opsonized by complement proteins. To test the hypothesis, we first investigated whether the dependency on time, temperature, and serum is indeed at the ligand (β-glucan) level or at the receptor (CR3) level. To discern the influence of serum, time, and temperature on the ligand versus the receptor, we designed an experimental set-up where the β-glucan was pre-treated with serum, added to the cells that were resuspended in HI serum, and then subsequently measured rescue of binding to the cells. Note that conditions using HI serum were shown in FIG. 3a to be non-permissive for binding. in these pre-treatment of β-glucan experiments, the β-glucan:serum ratio was given careful consideration so as to keep the ratio in the same range as was found to be optimal in the binding scenario, where the β-glucan, cells, and serum were mixed together at one time. Also, the percentage of regular serum carried over along with the pre-treated glucan was kept under 3%.

Figure 5A:
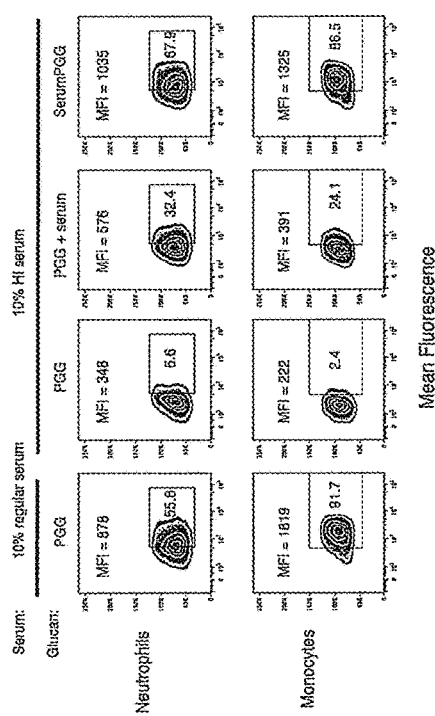
FIG. 5. Requirement of optimal percentage of serum, incubation time, and incubation temperature at the ligand level versus the cellular level Binding of PGG β-glucan to cells in non-permissive binding conditions including cells resuspended in HI serum, short period of incubating β-glucan with cells, or low incubation temperature was measured after addition of β-glucan pre-treated with serum. For serum pre-treatment of β-glucan, β-glucan at a concentration of 60 mg/mL was incubated with 90% serum at 37° C. for 30 minutes in order to obtain an optimal glucan to serum ratio and to keep the percentage of serum carried over under 3%. A) β-glucan treated with PBS (PGG), or β-glucan and serum added separately (PGG+serum), or serum pre-treated β-glucan (SerumPGG) were added to a concentration of 200 μg/mL to neutrophils or at 100 μg/mL to PBMC, incubated for two hours at 37° C. in media containing 10% regular serum or 10% HI serum, and then binding was measured as described in Material and Methods. Binding of SerumPGG to cells in HI serum was comparable to that observed in regular serum, while minimal rescue of binding was observed with β-glucan that was not treated with serum (PGG and PGG+serum). B) Binding was measured after incubating PGG or SerumPGG with the cells for either 10 minutes or two hours at 37° C. in media containing either 10% regular serum or 10% HI serum. SerumPGG bound within 10 minutes of incubation with cells in HI serum as opposed to measureable binding observed only after an hour of incubating the PGG with cells in regular serum. C) Binding was measured after incubating PGG or SerumPGG with cells for two hours at either 37° C. or 4° C. with cells in media containing either 10% regular serum or 10% HI serum. In contrast to minimal binding of PGG to cells in regular serum at 4° C., SerumPGG showed effective binding to cells in HI serum at 4° C. Data shown in the faun of zebra plots with MFI and percentage of BfD IV positive population stated is representative of three experiments performed with cells obtained from three different donors.
Figure 5C:
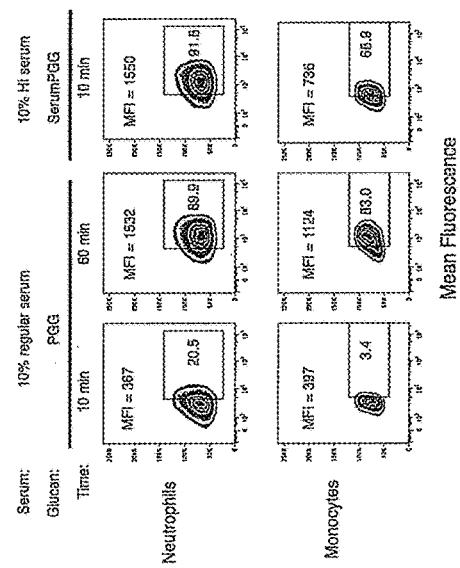
Figure 5B:
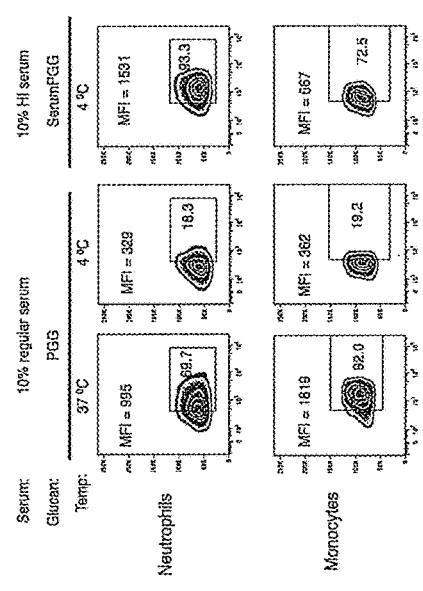

Results in FIG. 5a show that once the soluble β-glucan was pre-treated with serum at 37° C. for 30 minutes and then added to cells, binding was completely rescued. While the extent of rescued binding as measured by MFI and the percentage of cells positive for BfD IV staining was minimal for untreated β-glucan (PGG) and β-glucan plus serum added separately to the cells (PGG+serum), the binding obtained by using serum pre-treated PGG (SerumPGG) was comparable to that observed for cells cultured with β-glucan in 10% regular serum. The pre-treated β-glucan exhibited binding to neutrophils and monocytes in HI serum within 10 minutes of incubation, which otherwise was shown in FIG. 3b to occur in 30-60 minutes for neutrophils and 60-120 minutes for monocytes (FIG. 5b). Furthermore, the serum pre-treated β-glucan could even recover binding on cells incubated at 4° C. in HI serum, which again was demonstrated in FIG. 3c as a condition that allows minimal binding (FIG. 5c).

These results demonstrate that serum, time, and temperature are critical factors for β-glucan binding to cells from the ligand (PGG β-glucan) perspective, and do not appear to be relevant factors for CR3 modulation.

Opsonizing Soluble PGG β-glucan Occurs by Covalent Interaction of Complement Proteins with the β-glucan After demonstrating the prerequisite of serum interacting with PGG β-glucan in order for cells to bind the β-glucan, we further investigated complement opsonizing of β-glucan by determining the actual interaction between the β-glucan and one of the major complement opsonins, iC3b, which is also a ligand of CR3 receptor.

Figure 6A:
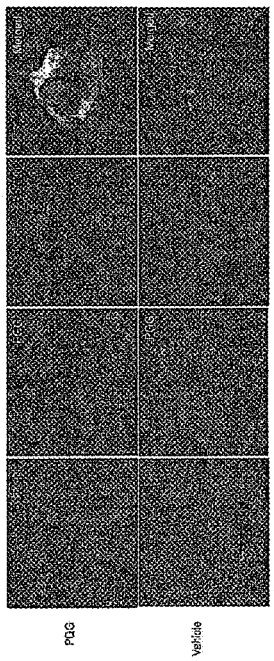
FIG. 6. Detecting complement opsonin, iC3b on the surface of PGG β-glucan-bound cells In order to investigate whether PGG β-glucan was being complement opsonized, the presence of iC3b on β-glucan-bound cells and also directly to β-glucan in a cell-free system was determined. A) Staining of neutrophils and monocytes for β-glucan by BfD IV and iC3b by a monoclonal antibody specific for the neo-epitope of iC3bis shown. Human neutrophils or PBMC were incubated with 200 μg/mL and 100 μg/mL of PGG β-glucan respectively at 37° C. for two hours, stained for BfD IV and anti-iC3b, and analyzed by flow cytometry as described in Material and Methods. The histograms show the fluorescence intensity of BfD IV and anti-iC3b stained cells treated with PGG β-glucan (solid) in comparison to that of the vehicle-treated (gray filled) control group. Shown here is data representative of three independent experiments from three different donors. B) Co-localization of PGG β-glucan and iC3b on neutrophils was then evaluated by confocal microscopy. PGG β-glucan-treated (upper panel) and vehicle-treated neutrophils (lower panel) were double stained with BfD IV and the anti-iC3b monoclonal antibody. Individual neutrophil was identified with the nuclei stain DAPI (blue), BfD IV antibody bound to glucan was detected by Cy5 labeled anti-IgM secondary antibody (pseudocolored green), and anti-iC3b monoclonal antibody bound to iC3b on the cells was detected by Cy3 labeled anti-IgG secondary antibody (red). The merged stains of BID IV and anti-iC3b stains (yellow) demonstrate co-localization of iC3b and PGG β-glucan on the surface of neutrophils. Original magnification for all the images is 100X. The microscopy data is representative of two independent experiments from two different donors. C) The direct interaction of iC3b and glucan was also evaluated in a cell-free system using ELISA. PGG β-glucan or dextran at concentration 300 μg/mL was immobilized to a plate and incubated with regular or HI serum for 30 minutes at 37° C. The plate was then probed for β-glucan-bound iC3b using the anti-iC3b monoclonal antibody as described in Material and Methods. Fold change was calculated as optical densities of β-glucan-treated wells divided by that of the blank wells with no immobilized glucan. The graph plotted with the mean fold change values ±SEM from three separate experiments indicate iC3b deposition on PGG β-glucan treated with regular serum group versus significantly less iC3b detected on β-glucan treated with HI serum or dextran treated with regular serum groups. **$p \leq 0.05$ compared with PGG β-glucan-treated with regular serum group. D) For pull-down experiments, PGG β-glucan was treated with serum as described for FIG. 5, and then incubated with BfD IV at room temperature for 30 minutes. β-glucan from the β-glucan-serurn-BfD IV mixture was immunoprecipitated using rat anti-mouse anti-IgM beads. The beads with the immunoprecipitated material were then subjected to flow cytometry for detecting iC3b using FITC-labeled anti-iC3b Ab. The histogram shows the comparison of iC3b detected on various β-glucan-treated groups (solid) in comparison to that of the vehicle-treated group (gray filled). The data shows the presence of iC3b on PGG β-glucan immunoprecipitated from regular serum, but not when immunoprecipitated from HI serum. Dextran, which has no reactivity to BID IV, did not pull-down iC3b. Data shown here is representative of two independent experiments from two different donors. E) The involvement of covalent interaction of complement with PGG β-glucan was assessed by inhibiting iC3b deposition and binding to cells subsequent to inhibiting the covalent binding capacity of complement proteins by 0.67% methylamine (MA) treatment of the serum. As shown in the graph, MA treatment of serum completely abrogated iC3b deposition on immobilized glucan. The histograms demonstrate that in comparison to binding in the presence of serum that have gone through the process identical to MA treatment (solid), binding in the presence of MA-treated serum (dotted) was completely inhibited to the level obtained in the vehicle treated group (gray filled). The data, representative of two experiments demonstrate (a) that covalent interaction of complement with PGG β-glucan is critical for iC3b opsonization and (b) binding of β-glucan to both neutrophils and monocytes.

First, we evaluated whether iC3b can be detected on the β-glucan-bound neutrophils and monocytes. Results shown in FIG. 6a demonstrate increased staining of iC3b on monocytes and neutrophils incubated with β-glucan in 10% serum in comparison to iC3b staining levels on cells incubated in 10% serum alone with no β-glucan.

Figure 6B:
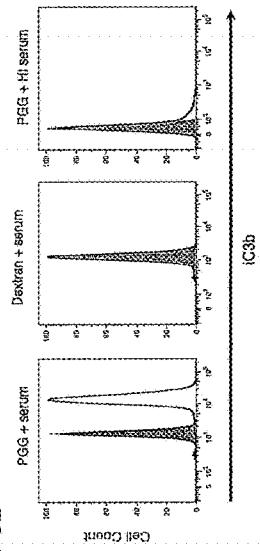

We next determined whether the β-glucan and iC3b co-localize on β-glucan-bound cells by confocal microscopy. Results presented in FIG. 6b show detecting β-glucan and iC3b on neutrophils using BfD IV and monoclonal antibody against iC3b, respectively. Both fluorophores are visually brighter on the β-glucan-treated cell versus vehicle-treated cell. Merging of the BfD IV and iC3b monoclonal antibody images indicates that the bound glucan and iC3b protein are co-localized on neutrophils.

The results from confocal microscopy were further corroborated by evaluating the physical interaction of PGG β-glucan with iC3b in two ways. First, we used a solid phase immunoassay system where the β-glucan was immobilized to a solid phase, incubated with serum, and then iC3b that was captured by the β-glucan was detected by ELISA. Second, we also used immunoprecipitation in which β-glucan was immunoprecipitated in fluid phase from a mixture of the β-glucan incubated with serum, using the BfD IV as the immunoprecipitating antibody, and subsequently subjecting the immunoprecipitated reaction to flow cytometric detection of co-immunoprecipitated iC3b protein.

Figure 6D:
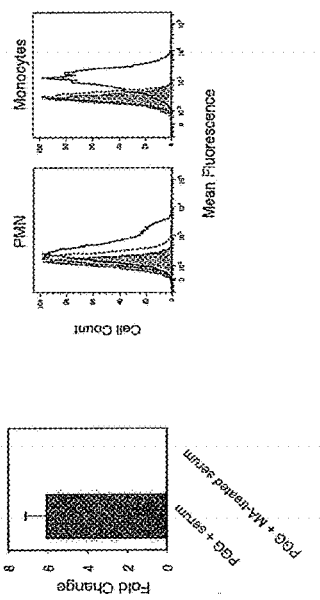
Figure 6C:
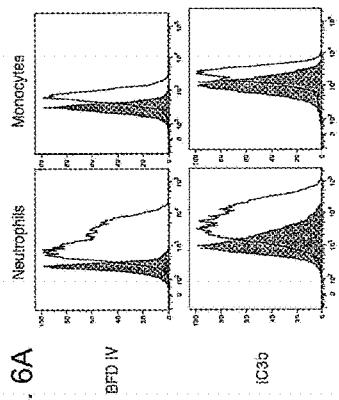

The results obtained from the ELISA showed that the fold increase of iC3b detected in wells with immobilized β-glucan compared to background was significantly higher than the fold increase on dextran-bound wells or wells with immobilized β-glucan incubated in HI serum (FIG. 6c). In the immunoprecipitation studies, iC3b protein was pulled-down along with the BfD IV-precipitated β-glucan, while no iC3b was detected when the β-glucan was immunoprecipitated in HI serum. The absence of iC3b in the immunoprecipitate from dextran-serum mixture indicated that the iC3b interaction was specific to PGG β-glucan (FIG. 6d).

Figure 6E:
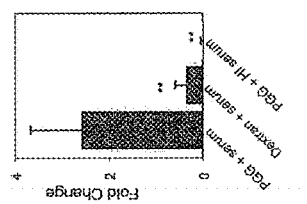

The nature of the physical interaction between PGG β-glucan and iC3b complement protein also was examined. Methylamine has been traditionally used to investigate the covalent binding capacity of complement proteins; methylamine is an amine that covalently binds to the reactive thioester site of C3b and inhibits the forming of a covalent bond between C3b and the reactive surface on the pathogens (Howard J B 1980). We hypothesized that iC3b covalently interacts with the hydroxyl groups of PGG β-glucan and, thus, that methylamine treatment of serum should abrogate iC3b interaction with the β-glucan, which ultimately should inhibit binding of the glucan on human immune cells. FIG. 6e shows complete inhibition of iC3b deposition on the immobilized β-glucan incubated with methylamine-treated serum. Methylamine-treated serum also abrogated the ability of PGG β-glucan to bind to cells as compared to regular serum conditions. Thus, these data provide evidence that soluble PGG β-glucan becomes opsonized when incubated with serum by forming a covalent bond with one of the complement opsonins, iC3b, and that opsonization is involved in binding of the β-glucan to neutrophils and monocytes.

Classical and Alternative Pathways of Complement Activation are Involved in Opsonizing Soluble PGG β-glucan In order to evaluate the role of classical or alternative pathway in opsonizing PGG β-glucan, we employed differential chelating of divalent cations that are known to be involved in one or both of the pathways. Divalent cations are required for specific steps in complement activation: calcium-dependent assembly of C1 complex for initiating classical pathway, and magnesium-dependent formation of C3 convertase, the enzyme required for amplifying the alternative pathway (Lepow IH 1963, Gotze O 1971, Pillemer L 1954,). While EGTA treatment of serum completely blocks activating the classical pathway by chelating calcium ions, it allows sub-optimal activating of alternative pathway by causing depleting magnesium ions. Adding magnesium ions in a concentration equimolar to EGTA (MgEGTA serum) allows optimal complement activation by the alternative pathway while completely inhibiting the classical pathway (DesPrez RM 1975).

Figure 7B:
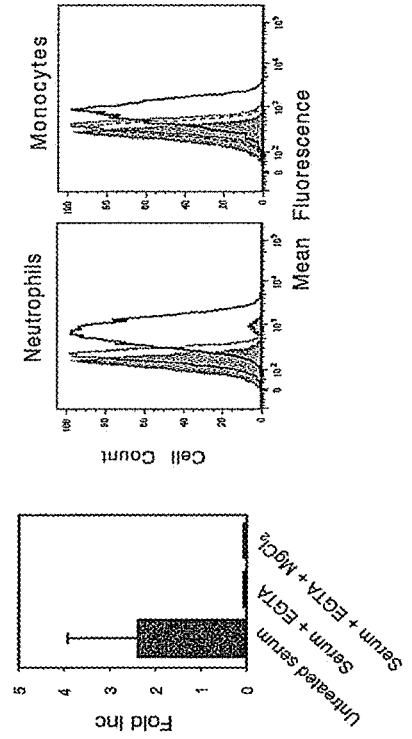
FIG. 7. Role of classical pathway and alternative pathway in binding of PGG β-glucan to neutrophils and monocytes The role of classical and alternative pathways (CP and AP) of complement activation in opsonization and binding of PGG β-glucan was evaluated by using serum in the presence of cations that are differentially used by both the pathways or in the presence of pathway specific blocking antibody. A) The ability of EGTA-treated serum (10 mM) to block both sensitized sheep erythrocytes (SRBC)-activated CP and cobra venom factor (CVF)-activated AP, and MgEGTA-treated serum (10 mM EGTA+10 mM $MgCl_2$) to block CP while allowing AP to function was evaluated by measuring the forming sC5b-9 complex in the serum of various treatment groups as per the method described in the Material and Methods section. Data are expressed as mean±SEM from two separate experiments. B) iC3b deposition on immobilized PGG β-glucan and binding of PGG β-glucan to neutrophils and monocytes in the presence of untreated, EGTA-treated or MgEGTA-treated serum was measured as described previously. In the presence of EGTA- and MgEGTA-treated serum, minimal iC3b was detected on the glucan. The histograms show binding of PGG β-glucan to neutrophils and monocytes in the presence of media containing 10% untreated (solid), EGTA-treated (dashed), or MgEGTA-treated serum (dotted). Binding was completely inhibited in EGTA-treated serum, while MgEGTA-treated serum did not rescue it. C) Before evaluating the effect of specifically inhibiting the alternative pathway by blocking Factor D using anti-Factor D monoclonal antibody, the validity of the antibody was evaluated by measuring its ability to block CVF-activated AP, but not the SRBC-activated CP using sC5b-9 kit as per the method described in A. D) Binding of PGG β-glucan to neutrophils and monocytes were measured using serum with either anti-Factor D monoclonal antibody, or isotype control antibody. The histogram shows partially inhibited binding in media containing 10% serum treated with 20 µg/mL of anti-Factor D as compared to binding in the presence of serum treated with equal concentration of isotype control. These data suggest that both classical and alternative pathway play a role in complement opsonization and binding of PGG β-glucan to human neutrophils and monocytes.
Figure 7D:
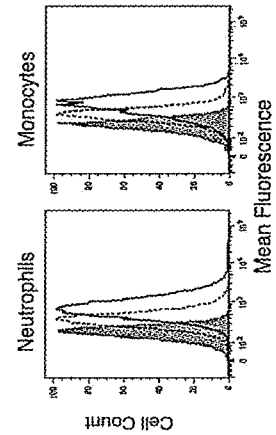
Figure 7A:
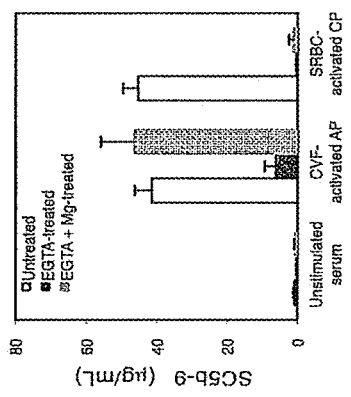

Prior to evaluating EGTA and MgEGTA-treated serum in binding studies with PGG β-glucan, the effects of the treated serum on the classical and alternative pathway were assessed. Sensitized sheep erythrocytes (SRBC) and cobra venom factor (CVF), the prototypical activators of the classical and the alternative complement pathways, respectively, were used to activate untreated, EGTA-treated, and MgEGTA-treated serum. The formation of fluid phase MAC (sC5b-9 complex) was assessed using a commercially available kit. EGTA treatment of the serum completely blocked both the classical and alternative pathways to background levels, while in MgEGTA-treated serum, the classical pathway remained inhibited and the alternative pathway functioned comparable to that in the untreated serum (FIG. 7a).

We then measured iC3b deposition on immobilized β-glucan and binding on cells using the untreated, EGTA-treated, or MgEGTA-treated sera. As shown in FIG. 7b, iC3b deposition on plate-bound β-glucan was completely inhibited in both EGTA-treated and MgEGTA-treated serum. The binding ability of PGG β-glucan pre-opsonized with untreated, EGTA-treated, or MgEGTA-treated serum to cells in HI serum was also evaluated. As EGTA could have the potential of blocking ions required for the function of CR3 receptor, the ability of the carried-over EGTA to block binding to cells in media with regular serum was also assessed. Any inhibition of binding in regular serum by EGTA carried over from pre-treatment was attributed to probable blocking of CR3 receptor. Pre-opsonizing PGG β-glucan in untreated serum allowed binding to occur in HI serum, while the rescue of binding was diminished in both EGTA and MgEGTA-treated serum. The carried over EGTA did not affect binding of β-glucan on cells in regular serum indicating that the inhibition effect was specifically due to the abolished complement activity and not due to blocking of CR3 function.

Figure 7C:
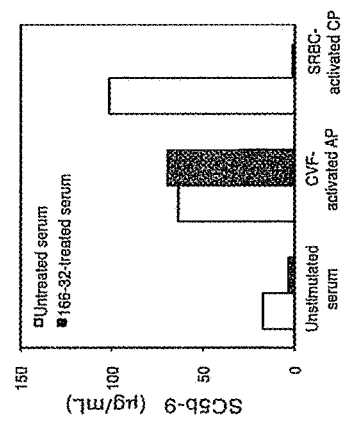

We then investigated the effect of the alternative pathway in the context of an intact classical pathway on binding by specifically blocking Factor D, a protease involved in the alternative pathway. The efficacy and specificity of 166-32, the anti-Factor D monoclonal antibody, was first evaluated by assessing its ability to block the CVF-activated alternative pathway but not the SRBC-activated classical pathway (FIG. 7c). Binding of PGG β-glucan to neutrophils and monocytes was then evaluated using serum treated with either anti-Factor D or isotype control antibody. Interestingly, as shown in FIG. 7d, blocking of the alternative pathway inhibited binding of the β-glucan to both neutrophils and monocytes. These data, taken together suggest that classical pathway is essential, and the alternative pathway is necessary but not sufficient for opsonization and binding of PGG.

Because all forms of yeast-derived β-glucans are fungal PAMPs, understanding the interaction of particulate yeast β-glucans and soluble yeast β-glucans with human innate immune cells is fundamental to the use of the β-glucans for any therapeutic purpose. In this study, we investigated the binding characteristics of *Saccharomyces cerevisiae*-derived, pure, and analytically well-characterized soluble PGG β-glucan to human neutrophils and monocytes. This investigation demonstrated that CR3 is the main receptor on human innate immune cells for PGG β-glucan and that the binding of soluble β-glucan to CR3 is complement-dependent.

Concentration dependent binding of β-glucan on neutrophils and on monocytes was detected either indirectly using BfD IV, a monoclonal antibody specific for β-glucan, or directly using DTAF-labeled β-glucan (FIG. 1). BfD IV has been previously shown to be specific for β-(1,3)-linked glucans and β-(1,6)-linked glucans and also has been used to detect β-glucan within live intact yeast (Milton 2001 and Lavigne LM 2006). The minimum concentration off β-glucan detected on the cells by the BfD IV detection system 100 µg/mL, while a concentration as low as 25 µg/mL was detected by DTAF labeling (FIG. 1b). Even though detecting bound β-glucan using DTAF labeling was somewhat more sensitive, BfD IV detection system was employed for all the binding studies in order to avoid labeling inconsistencies from batch to batch. DTAF-labeled β-glucan was shown to bind the cells in a saturable manner that was blocked by excess unlabeled PGG β-glucan (FIG. 1c).

The role of complement proteins in binding of PGG β-glucan to human neutrophils and monocytes was elucidated in several different ways. Dependency of binding on the serum content in the media (FIG. 3a) and inhibiting binding in the presence of heat-inactivated serum (FIG. 4a) were the first indicators that serum heat-labile proteins may be involved in binding. Significant β-glucan binding inhibition in the presence of compstatin-treated serum further helped confirm the involvement of specific serum complement proteins (FIG. 4b). Compstatin, by selectively binding to C3, can inhibit all complement activation pathways by inhibiting C3 convertase-mediated cleavage of C3 into its activated form C3b, which then inhibits downstream steps of the complement pathways from being activated (Ricklin D, 2008). These results indicated that the breakdown of C3 into active complement components was required for binding of β-glucan. Binding of PGG increased as a function of time and/or temperature of incubation with cells (FIGS. 3b and 3c). Pre-opsonizing PGG β-glucan allowed binding to occur on the cells in HI serum at 4° C. in 10-30 minutes, which are typical conditions for ligand binding (FIG. 5). Pre-opsonizing PGG itself also was found to be dependent on serum time and/or temperature, meaning that binding to cells was increased as the serum content, the incubation time, and/or the incubation temperature of the PGG-serum pre-opsonization mixture increased.

Complement-mediated opsonization involves depositing C3 fragments on the surface of microorganisms. The actual chemistry involved in complement-mediated opsonization has been demonstrated to involve a covalent ester or an amide bond between the acyl group of an active thioester site in C3b and its breakdown products—including iC3b with hydroxyl groups of carbohydrates or amine groups of proteins present on the surface of pathogens (Law SK 1980, Gadjeva M 1998). The complement fragments—specifically, C3b and iC3b bound to β-glucan have been detected on zymosan and intact yeast (Cain J A 1987, Boxx G M 2010, Ezkowitz R A, 1985). Opsonized PGG β-glucan was identified by detecting iC3b complement protein bound to a β-glucan-bound cell and/or bound to β-glucan itself using a monoclonal antibody specific for iC3b (FIG. 6a-d). Disrupting the thioester bond in C3 by MA treatment rendered the serum incapable of allowing the depositing of iC3b on immobilized β-glucan and the binding of PGG β-glucan on cells, highlighting the covalent nature of interaction between complement proteins and hydroxyl groups of PGG (FIG. 6e).

Yeast-induced immune responses in human monocytes and neutrophils was shown to be inhibited by one of the ligands of I domain of CR3, fluid-phase iC3b. This indicated that blocking the I domain can sterically block the lectin site involved in binding β-glucan. The interaction between opsonized yeast and CR3 on human neutrophils was demonstrated to involve the binding of fixed iC3b to the I domain and the binding of β-glucan to the lectin domain of CR3. This study also showed that blocking both the I domain and the lectin domain of CR3 failed to significantly inhibit binding of opsonized yeast, but did manage to inhibit functional responses. Unlike the binding of opsonized particulate β-glucan, binding of low molecular weight soluble zymosan polysaccharide (SZP) β-glucan to cells that express recombinant fragments of CR3 was significantly inhibited in the presence of 10% FBS using monoclonal antibodies to either the lectin domain or the I domain. SZP β-glucan binding to the CR3 fragment containing the lectin domain did not require heterodimerization with the CD 18 chain. In our study, when both the I domain and lectin domain of CR3 were blocked, there was no significant inhibition of binding of soluble opsonized β-glucan to human neutrophils and/or monocytes (FIG. 2). However, maximum binding inhibition was consistently achieved by blocking the CD 18 chain along with the CD11b chain. These data reflect the involvement of the CD18 chain in allowing the CD11b chain to attain a conformation that is conducive to binding either or both of the iC3b component and the β-glucan component of opsonized PGG β-glucan.

Our results provide data supporting the requirement of both the classical pathway and the alternative pathway of complement activation for opsonization and subsequent binding of soluble β-glucan to human immune cells (FIG. 7). The activation of the classical pathway by soluble β-glucan may be antibody-dependent or antibody-independent. Because activating and amplifying the alternative pathway can involve factor D, and because blocking factor D effectively reduced binding of β-glucan, the β-glucan may initially activate the classical pathway, and the nascent C3b then may feed into the alternative pathway to further amplify complement activation. We investigated the extent of amplification of complement activation by measuring fluid phase MAC complex in serum treated with PGG β-glucan. The soluble PGG β-glucan did not activate formation of terminal complement complexes, while particulate β-glucan clearly did. These results are consistent with either cell-bound PGG β-glucan or free PGG β-glucan providing a surface where complement activation occurs to some extent, but then becomes accessible to complement regulators such as, for example, Factor I, Factor H, CR1, or membrane complement regulatory protein that prevents the activation pathway to go to completion (unpublished observations). This observation is consistent with findings in clinical settings where intravenous administration of soluble β-glucans has been associated with few side effects, while the administration of particulate β-glucans can induce inflammatory responses (Deimann W 1980, Kilgore KS 1997, Cleary JA 1999).

Figure 8:
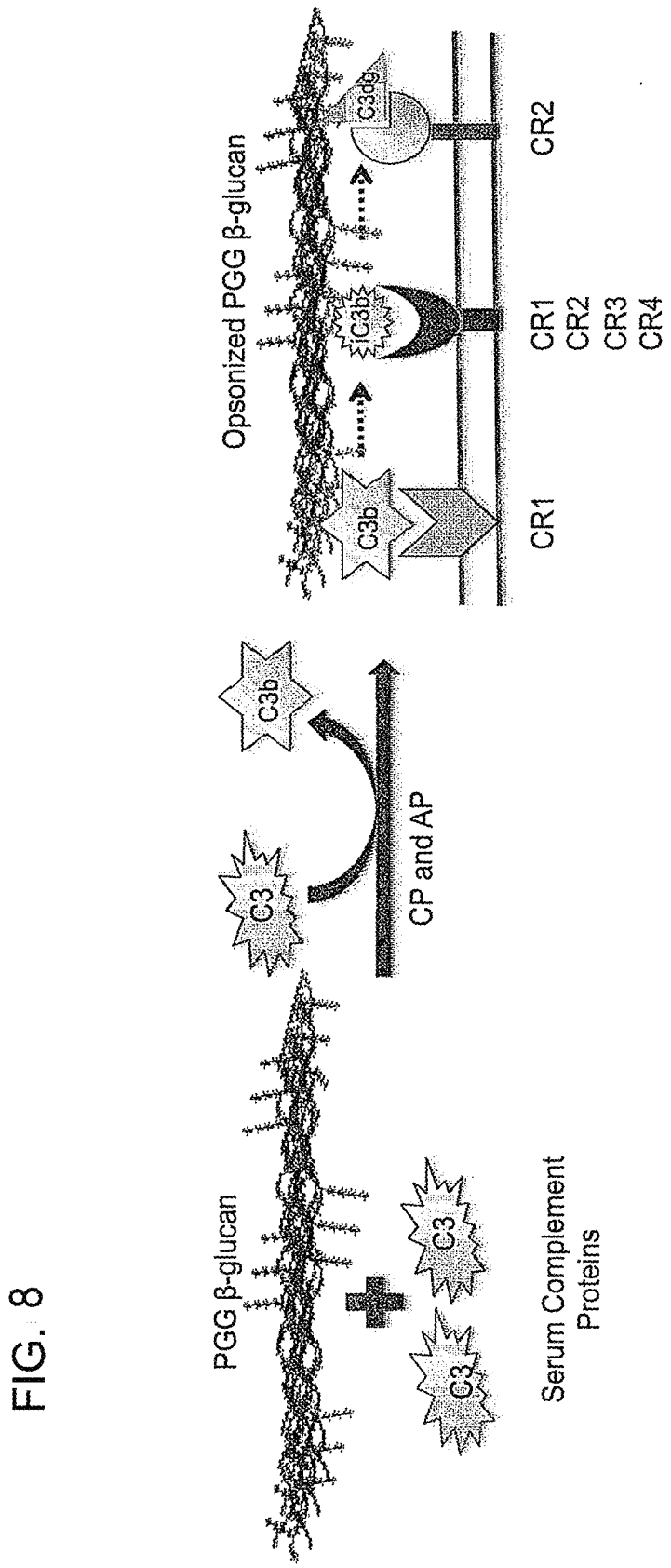
FIG. 8 is a schematic diagram illustrating an exemplary route of opsonizing soluble β-glucan (PGG β-glucan) and an exemplary interaction of the opsonized soluble β-glucan with immune cell receptors.

In summary, our study is the first to demonstrate the role of complement in binding of soluble yeast β-glucan to human innate immune cells. The discovery of ability of soluble yeast β-glucan to activate complement pathways and become opsonized expands the horizon for its immunomodulatory activities as the soluble β-glucan may be recognized by several complement receptors on the repertoire of human innate and adaptive immune cells (FIG. 8). The results of this investigation could have implications on the design of basic research as well as clinical research studies, including studies to further the understanding of mechanism of action, biomarker identification, and more importantly, the clinical application of soluble yeast β-glucan in patient populations with either genetic deficiency or malfunctional CR3 receptor or complement system.

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments. For any method disclosed herein that includes discrete steps, the steps may be conducted in any feasible order. And, as appropriate, any combination of two or more steps may be conducted simultaneously.

As used herein, the team "and/or" means one or all of the listed elements or a combination of any two or more of the listed elements; the terms "comprises" and variations thereof do not have a limiting meaning where these terms appear in the description and claims; unless expressly indicated otherwise, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

The present invention is illustrated by the following examples. It is to be understood that the particular examples, materials, amounts, and procedures are to be interpreted broadly in accordance with the scope and spirit of the invention as set forth herein.

EXAMPLES

Example 1

Material and Methods
Antibodies (Abs) and Reagents

Mouse IgG1, IgG2a, isotype control Abs, anti-CD3, anti-CD11a (HI111), and anti-CD11b Ab (LM2/1) were purchased from eBioscience (San Diego, Calif.). Cy3-conjugated goat anti-mouse IgG, anti-CD14, and CD15 Abs were from BioLegend (San Diego, Calif.). Anti-CD11b Ab (VIM12) and rat anti-mouse IgM Dynabeads were from Invitrogen (Camarillo, Calif.). Anti-CD 18 Abs (IB4) were from Abcam (Cambridge, Mass.) and Ancell (Bayport, Minn.), respectively. Anti-Dectin-1 Ab (GE2) was from AbD Serotec (Raleigh, N.C.). The generation and specificity of Biothera owned β-1,3/1,6-glucan-specific monoclonal antibody BfD IV (clone 1006) has been described previously (30). Complement factor D (ID)-specific Ab (166-32) was from ATCC (Manassas, Va.). FITC-conjugated F(ab')2 goat anti-mouse IgM and Cy5-conjugated goat anti-mouse IgM Abs were purchased fro Jackson ImmunoResearch Lab (West Grove, Pa.). FITC-conjugated goat anti-human complement C3 Ab was from MP Biomedicals (Solon, Ohio). Anti-iC3b (neo-antigen) Ab, Cobra venom factor (CVF), CH50 Eq EIA kit and SC5b-9 Plus EIA kit were from Quidel (San Diego, Calif.). Compstatin (ICVVQD-WGHHRCT (SEQ ID NO:1)) and control peptide (IAV-VQDWGHHRAT (SEQ ID NO:2)) were from Tocris Bioscience (Bristol, UK). Dextran, laminarin, EGTA, $MgCl_2$, methylamine, human serum albumin (HSA), bovine serum albumin (BSA) and DAPI were from Sigma-Aldrich (St. Louis, Mo.).

Preparation and Characterization of PGG β-glucan

The pharmaceutical grade PGG β-glucan, the soluble β-1,3/1,6 glucan is manufactured as described in U.S. Patent Application Publication No. US2008/0103112 A1. Analytical characterization of PGG included nuclear magnetic resonance (NMR) spectroscopy, Fourier transform infrared (FTIR) spectroscopy, size exclusion chromatography (SEC), multiple angle light scattering (MALLS), and differential refractive index (DRI) detection. PGG β-glucan was finally prepared for use by performing a buffer exchange into phosphate-buffered saline (PBS) using 3K molecular weight cut off (MWCO) Amicon centrifugal filtration units (Millipore, Billerica, Mass.). Dextran and laminarin were prepared by dissolving the required amount in Dulbecco's phosphate-buffered saline (DPBS).

For 5-(4,6-Dichlorotriazinyl) aminofluorescein (DTAF)-labeling of PGG β-glucan, 100 moles of glucose was labeled with approximately 1 mole of fluorescein. The degree of labeling was determined using an ε of 68,000 $M^{-1} cm^{-1}$ at 494 nm along with the concentration of β-glucan. Labeling was performed by treating a solution of approximately 5 mg/mL β-glucan in 0.02 M aqueous sodium carbonate with DTAF (Invitrogen, Camarillo, Calif.) as a 5 mg/mL DMSO solution at a ratio of 0.1 mg DTAF per milligram of β-glucan for 18 hours. The reaction mixtures were concentrated and then re-diluted with PBS four times using 3K MWCO centrifugal filtration units. Unbound label was scavenged by treatment of 5 mg/mL solutions of β-glucan with ethanolamine (approximately 3 mg ethanolamine per mg β-glucan) for 18 hours followed by four additional PBS exchanges (as above). All labeled and unlabeled β-glucans were sterile filtered using a 0.2 μm filter and tested for endotoxin (PYROGENE from Lonza Group Ltd, Basel Switzerland). The measured endotoxin levels were less than 0.05 EU/mL. The hexose concentration of the β-glucan preparations was determined by the anthrone method (Bailey R W, 1958).

Isolation of Human PBMC and Neutrophils

Heparinized venous blood was obtained from healthy individuals with informed consent as approved by the Institutional Review Board. Briefly, PBMC were isolated by Ficoll-Paque (Amersham Biosciences, Piscataway, N.J.) density gradient centrifugation. Neutrophils were subsequently enriched by sedimentation with 3% dextran, followed by hypotonic lysis of residual erythrocytes. The purity and viability of neutrophils and PBMC obtained were consistently greater than 95%.

Preparation of Human Autologous Serum

Human serum was prepared according to vendor's instruction. 10 mL of non-heparinized whole blood was added to a VACUTAINER SST™ tube (Becton Dickinson, Franklin Lakes, N.J.). The tube was incubated at room temperature with constant rotation for 30 minutes, centrifuged at 2000 rpm (approximately 1150×g) for 10 minutes, and the cleared serum was collected.

Binding Studies Using PGG β-glucan

Binding of PGG β-glucan at Various Concentrations

Enriched neutrophils or PBMC were resuspended at $1 \times 10^6$ cells/mL in RPMI 1640 supplemented with 10% serum. PGG β-glucan at hexose concentrations 100 μg/mL, 200 μg/mL, or 400 μg/mL were added to neutrophils or PBMC and incubated in a 37° C., 5% $CO_2$ humidified incubator for two hours. After incubation, cells were washed twice with FACS buffer (HBSS supplemented with 1% FBS and 0.1% sodium azide) to remove any unbound β-glucan, and subsequently treated with Fc block (Miltenyi Biotec, Auburn, Calif.). After the Fc block step, cells were stained with the BfD IV Ab for 30 minutes at 4° C. and washed twice with cold FACS buffer. Cells were then incubated with FITC-conjugated $F(ab')_2$ goat anti-mouse IgM for 30 minutes at 4° C. and washed once with cold FACS buffer before fixing with 1% paraformaldehyde.

In early optimization experiments, neutrophils, monocytes, and T cells were identified by staining with fluorescently labeled anti-CD 15, anti-CD 14, or anti-CD3 Abs, respectively. Events were collected on a LSRII flow cytometer (BD Biosciences, San Jose, Calif.) and analysis was performed using FLOWJO (Tree Star, Ashland, Oreg.). For assessing binding of DTAF-labeled PGG β-glucan to human neutrophils, 25 βg/mL, 100 μg/mL, or 400 μg/mL of labeled β-glucan was added to neutrophils resuspended in RPMI/10% serum, incubated in a 37° C., 5% $CO_2$ humidified incubator for one hour, washed twice with cold FACS buffer, and fixed with 1% paraformaldehyde. Surface binding of DTAF-conjugated β-glucan was subsequently assessed by flow cytometric analysis. To determine receptor-specific binding, binding of 25 μg/mL of DTAF-labeled PGG β-glucan was assessed by incubating the labeled β-glucan with the cells in the presence of 10 mg/mL of unlabeled PGG β-glucan or dextran.

Binding of PGG β-glucan after Receptor Blocking

For experiments that involved blocking the CR3 receptor or Dectin-1 receptor, the cells were pre-incubated with specific receptor-blocking antibodies or the relevant isotype control at 4° C. for 30-45 minutes. PGG β-glucan was added (200 μg/mL to neutrophils and 100 μg/mL to PBMC) and binding was measured as described above. To block binding to CR3, we used LM2/1 (a mouse anti-human IgG1 monoclonal antibody to the I domain of CD11b chain of CR3), VIM12 (a mouse monoclonal IgG1 anti-human antibody to the lectin domain of CD11b chain of CR3), and IB4 (a mouse monoclonal IgG2a anti-human antibody to the CD18 chain of CR3), each used at 10 μg/mL/$1 \times 10^6$ cells. The combinations of CR3 blocking antibodies used were either LM2/1+VIM12 to block both the I domain and lectin domains of the CD11b subunit or LM2/1+VIM12+IB4 to block both the CD11b and CD18 chains of CR3. HI111, the mouse monoclonal IgG1 anti-human antibody to the CD11a chain was used at 10 μg/mL as a negative control in some of the blocking experiments. For blocking Dectin-1 receptor, clone GE2, a mouse monoclonal IgG1 anti-human antibody was used at 10 μg/mL (AbD Serotec, Raleigh, N.C.). All the isotype controls were used at the same concentration as the blocking antibodies.

Binding Studies to Determine Serum, Time, and Temperature Dependency

The experiments to determine binding of PGG β-glucan at 200 μg/mL to neutrophils or at 100 μg/mL to PBMC were performed as described above with the following changes. For determining serum dependency, PGG β-glucan was incubated with neutrophils or PBMC resuspended in RPMI 1640 containing 2%, 5%, or 10% autologous serum at 37° C.

for two hours. For time-course experiments, PGG β-glucan at indicated concentrations was incubated with cells resuspended in 10% autologous serum at 37° C. for 10 minutes, 20 minutes, 60 minutes, or 120 minutes. For temperature dependency experiments, PGG β-glucan at indicated concentrations was incubated with cells resuspended in 10% autologous serum for two hours at 4° C., room temperature, or 37° C.

Binding of PGG β-glucan after Serum Pre-treatment

PGG β-glucan at concentration 60-80 mg/mL was incubated with human serum at 1:10 volume ratio for 30 minutes in a 37° C. water bath. The serum-pretreated PGG β-glucan was added to neutrophils at 200 µg/mL or to PBMC at 100 µg/mL resuspended in RPM1 containing either 10% regular autologous serum or 10% HI serum at indicated time and temperature of incubation. Binding was then determined as described previously.

Binding Studies to Determine the Role of Complement Proteins in Serum

To determine the role of complement proteins in binding, experiments were performed as described above except for using serum containing 10% HI, compstatin-treated or methylamine (MA)-treated, EGTA- or EGTA+MgCl2 (MgEGTA)-treated, or factor D-blocked serum. Heat-inactivated (HI) serum was prepared by incubating serum in a 56° C. water bath for 30 minutes. For compstatin- and control peptide-treated serum, compstatin or the control peptide was added to human serum at either 20 µM or 100 µM and incubated at room temperature for 10 minutes. Treatment of serum with methylamine (MA) was done by incubating serum with 0.67% of methylamine for 2.5 hours at 37° C., followed by three washes with DPBS using Amicon centrifugal filter unit with a 3K MW cut-off (Millipore, Billerica, Mass.). DPBS-treated serum was prepared in the same manner and used as control serum for MA-treated serum. For blocking of factor D in the serum, 166-32 at concentration 20 µg/mL was incubated with serum on ice for 30 minutes, and then used for binding studies. For binding experiments in the presence of EGTA or MgEGTA, serum was incubated with 10 mM EGTA with or without 10 mM MgCl2 for 10 minutes at room temperature. The untreated and EGTA/MgEGTA-treated serum was then used to pre-treat PGG and perform binding studies as described earlier.

iC3b Staining on PGG β-glucan-bound Cells

Binding of PGG β-glucan to neutrophils and PBMC was done as above. iC3b deposition on these cells was detected by staining with a neo-epitope specific anti-iC3b Ab and PE-conjugated goat anti-mouse IgG and analyzing by flow cytometry.

ELISA for iC3b Deposition on Immobilized PGG β-glucan

PGG β-glucan or dextran was immobilized on wells of a 96-well polystyrene plate (COSTAR, Coming, Inc., Lowell, Mass.) by drying the glucans at 50° C. followed by UV cross-linking. The glucan-coated plate was first blocked with 1% BSA before incubation with untreated serum or serum undergone various treatments as described in binding studies, diluted 1:2 with wash buffer (PBS/0.05% Tween-20) for 30 minutes at 37° C. After washing the serum from the plate, the bound iC3b was probed using the anti-iC3b monoclonal antibody followed by biotin-labeled goat anti-mouse IgG Ab. The amount of immobilized biotin-labeled antibody was determined using streptavidin peroxidase and TMB substrate solution (KPL, Gaithersburg, Md.). $OD_{450}$ of each well was measured with the spectrophotometer SpectraMAX 250 (Molecular Devices, Sunnyvale, Calif.). Fold change was calculated as $OD_{450}$ of wells containing immobilized β-glucan divided by $OD_{450}$ of wells containing no β-glucan, both incubated in the presence of treated or untreated serum.

Immunoprecipitation of PGG β-glucan

PGG β-glucan or dextran at concentration 60-80 mg/mL was incubated with regular or HI serum at 1:10 volume ratio for 30 minutes in a 37° C. water bath. BfD IV Ab was added to the serum/β-glucan mixture and incubated at room temperature for additional 30 minutes. Magnetic beads conjugated with rat anti-mouse IgM (DYNABEADS, Invitrogen, Camarillo, Calif.) were washed three times with DPBS and incubated with serum-PGG β-glucan-BfD IV mixture for another 30 minutes at room temperature. The beads were separated magnetically and iC3b pulled-down along with immunoprecipitated PGG was probed using FITC-conjugated complement C3 Ab by flow cytometer.

Measurement of Fluid-phase SC5b-9 Complex Formation in the Serum

The MicroVue SC5b-9 EIA kit was used to measure activation of the classical and alternative pathways of complement according to the vendor's instruction (Quidel Corp., San Diego, Calif.). Briefly, the serum, untreated or treated was mixed with PBS, Ab-sensitized sheep RBC (SRBC), or 20 units of CVF and added to plate wells pre-coated with anti-sC5b-9 monoclonal antibody. The plate was incubated at 37° C. for 60 minutes, followed by five washes with the provided wash buffer. The plate was then incubated with the provided SC5b-9 Plus Conjugate, which contained horseradish peroxidase-conjugated Ab specific for sC5b-9 at room temperature for 30 minutes. The plate was washed five times, incubated with the substrate for 15 minutes at room temperature to initiate the enzymatic reaction and subsequently quenched with the stop solution. $OD_{450}$ was measured using the spectrophotometer SpectraMAX 250. The concentration of fluid phase sC5b-9 present in the samples was determined from the standard curve generated with the provided sC5b-9 standards.

Confocal Microscopy

Enriched neutrophils, resuspended at $1 \times 10^6$ cells/mL in either RPMI supplemented with 20% serum or heat-inactivated serum, were mixed with PGG β-glucan before being applied to a 10 mm glass cover slip placed in the well of a 24-well plate. The plate was incubated in a 37° C., humidified 5% $CO_2$ incubator for one hour. Unbound cells and PGG β-glucan were removed by washing with warmed PBS, and bound cells were subsequently fixed in 1% formaldehyde at room temp for 15 minutes. Cells were blocked with FCR blocking agent prior to staining with BFD IV and anti-iC3b monoclonal antibody for 30 minutes at 4° C., and followed by the secondary staining antibodies Cy5-conjugated goat anti-mouse IgM and Cy3-conjugated goat anti-mouse IgG at 4° C. for 30 minutes. Cells were penneabilized with 0.1% ice-cold TritonX-100 for three minutes on ice, stained with DAPI on ice for five minutes before mounting onto slides. Images were analyzed and acquired with Olympus FluoView 1000 IX2 Inverted confocal microscope. Images were adjusted equally in Adobe Photoshop (Adobe Systems Inc., San Jose, Calif.).

Example 2

Figure 9:
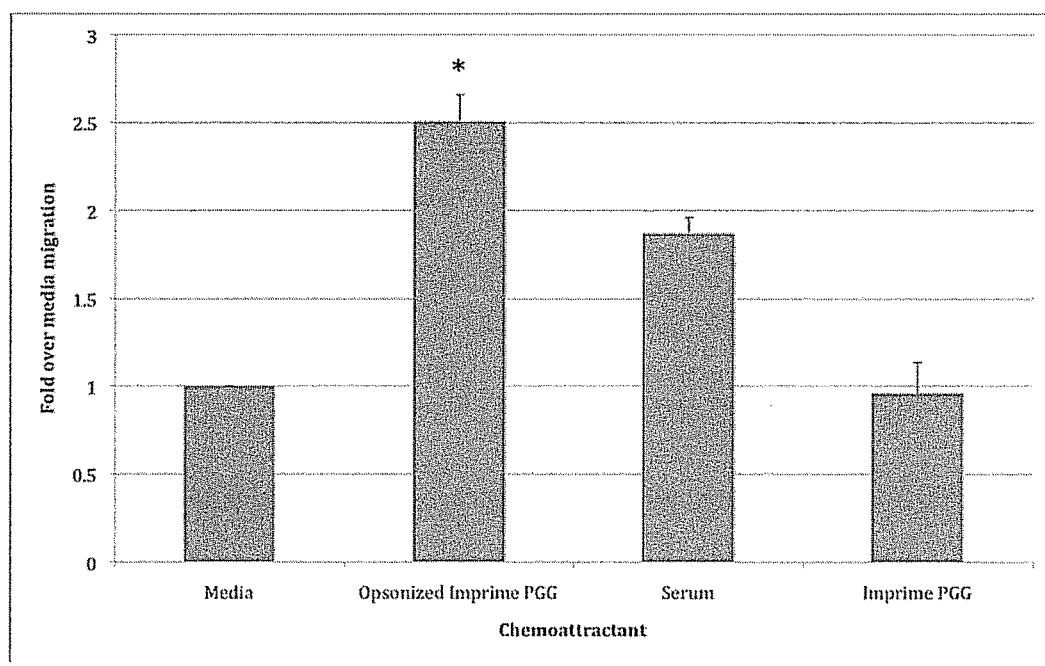
FIG. 9 is a bar graph showing enhanced migration of human neutrophils to opsonized soluble β-glucan.

Heparinized peripheral blood was obtained from healthy volunteers, and neutrophils were isolated by density gradient centrifugation with Ficoll-Paque followed by 3% dextrose sedimentation. Residual erythrocytes were removed by hypotonic lysis. Neutrophils were resuspended at 200,000 cells/mL in RPM with 3% autologous serum. Imprime PPG;

3.3 mg/mL and PBS control were mixed with the autologous serum in 1:1 ratio and placed in a 37° C. water bath for 30 minutes. After incubation, Imprime PGG was diluted in RPMI to achieve 200 µg/mL concentrations with final concentration of serum being 3%. PBS control was diluted in a similar manner. 31 µL of the diluted Imprime PGG or PBS control was added to three wells in the bottom of chemotaxis plates (Neuro Probe, Inc., Gaithersburg, Md.). Chemoattractants, C5a and IL-8 at 50 ng/mL served as positive controls (data not shown). The 8 µm chemotaxis membrane was applied to the plate and $6 \times 10^3$ number of neutrophils in 30 µL volume were added over each well containing chemoattractants. The plate was placed in a 37° C. incubator for one hour, lysed with 10 µL CELLTITER0GLO (Promega Corp., Madison, Wis.) and read for luminescence on an M5 plate reader (Molecular Devices, Inc., Sunnyvale, Calif.). Fold increase in migration over control media was calculated by dividing the RLU (relative luminescence units) for the treatment groups over migration to media (chemokinesis). Results are shown in FIG. 9.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

ICVVQDWGHHRCT SEQ ID NO: 1

IAVVQDWGHHRAT SEQ ID NO: 2

CITED DOCUMENTS

1. Cain J A et al., Role of complement receptor type three and serum opsonins in the neutrophil response to yeast. Complement. 1987; 4(2):75-86.
2. Ross G D et al., Specificity of membrane complement receptor type three (CR3) for beta-glucans. Complement. 1987;4(2):61-74.
3. Brown, G D et al., 2001. Immune recognition. a new receptor for beta-glucans. Nature, 413:36-37.
4. Brown G D et al., Dectin-1 is a major beta-glucan receptor on macrophages. J Exp Med. 2002 August 5; 196(3):407-12.
5. Taylor P R et al., Dectin-1 is required for beta-glucan recognition and control of fungal infection. Nat Immunol. 2007; 8:31-38.
6. Hong F et al., Mechanism by which orally administered beta-1,3-glucans enhance the tumoricidal activity of antitumor monoclonal antibodies in murine tumor models. J Immunol. 2004 July 15; 173(2):797-806.
7. Thornton BP et al., Analysis of the sugar specificity and molecular location of the beta-glucan-binding lectin site of complement receptor type 3 (CD11b/CD18). Journal of Immunology, 156:1235-1246, 1996.
8. Xia Y et al., Generation of recombinant fragments of CD11b expressing the functional beta-glucan-binding lectin site of CR3 (CD11b/CD18). Journal of Immunology, 162:7285-7293, 1999.
9. Vetvicka V et al., Soluble beta-glucan polysaccharide binding to the lectin site of neutrophil or natural killer cell complement receptor type 3 (CD11b/CD18) generates a primed state of the receptor capable of mediating cytotoxicity of iC3b-opsonized target cells. J Clin Invest. 1996; 98:50-56.
10. Hong F et al., Beta-glucan functions as an adjuvant for monoclonal antibody immunotherapy by recruiting tumoricidal granulocytes as killer cells. Cancer Res. 2003 December 15; 63(24):9023-31.
11. Li B et al., Yeast beta-glucan amplifies phagocyte killing of iC3b-opsonized tumor cells via complement receptor 3-Syk-phosphatidylinositol 3-kinase pathway. J Immunol. 2006 August 1; 177(3):1661-1669.
12. Brown et al., 2003. Fungal β-glucans and Mammalian Immunity. Imunity 19:311-315.
13. Brown G D. Dectin-1: a signalling non-TLR pattern-recognition receptor. Nat Rev Immunol. 2006 January; 6(1):33-43.
14. Walport M J. Complement. First of two parts. N Engl J Med. 2001 April 5; 344(14):1058-1066.
15. Walport M J. Complement. Second of two parts. N Engl J Med. 2001 April 12;344(15):1140-4.
16. Czop J K et al., 1985. Properties of glycans that activate the human alternative complement pathway and interact with the human monocyte beta-glucan receptor. J. Immunol. 135:3388-3393.
17. Fearon D T et al., 1977. Activation of the alternative complement pathway due to resistance of zymosan-bound amplification convertase to endogenous regulatory mechansims. Proc. Natl. Acad. Sci. U.S.A 74:1683-1687.
18. Pillemer L et al., The properdin system and immunity. I. Demonstration and isolation of a new serum protein, properdin, and its role in immune phenomena. Science. 1954 August 20; 120(3112):279-85.
19. Pillemer L et al., The properdin system and immunity. III. The zymosan assay of properdin. J Exp Med. 1956 January 1; 103(1):1-13.

20. Boxx G M et al., Influence of mannan and glucan on complement activation and C3 binding by *Candida albicans*. Infect Immun. 2010 March; 78(3):1250-1259
21. Sanchez-Madrid F et al., A human leukocyte differentiation antigen family with distinct alpha-subunits and a common beta-subunit: the lymphocyte function-associated antigen (LFA-1), the C3bi complement receptor (OKM1/Mac-1), and the p150,95 molecule. Journal of Experimental Medicine, 158:1785-1803, 1983
22. Ross G D et al., Membrane complement receptor type three (CR3) has lectin-like properties analogous to bovine conglutinin as functions as a receptor for zymosan and rabbit erythrocytes as well as a receptor for iC3b. J Immunol. 1985 May; 134(5):3307-3315.
23. Willment J A et al., Characterization of the human beta-glucan receptor and its alternatively spliced isoforms. J Biol Chem. 2001 Nov 23; 276(47):43818-43823.
24. Willment J A et al., The human beta-glucan receptor is widely expressed and functionally equivalent to murine Dectin-1 on primary cells. Eur J Immunol. 2005 May; 35(5):1539-1547.
25. Ujita M et al., Carbohydrate binding specificity of recombinant human macrophage beta-glucan receptor Dectin-1. Biosci Biotechnol Biochem. 2009 January; 73(1):237-240.
26. Palma A S et al., Ligands for the beta-glucan receptor, Dectin-1, assigned using "designer" microarrays of oligosaccharide probes (neoglycolipids) generated from glucan polysaccharides. J Biol Chem. 2006 Mar 3; 281(9):5771-5779.
27. Adams E L et al., Differential high-affinity interaction of Dectin-1 with natural or synthetic glucans is dependent upon primary structure and is influenced by polymer chain length and side-chain branching. J Pharmacol Exp Ther. 2008 Apr; 325(1):115-123.
28. Kennedy A D et al., Dectin-1 promotes fungicidal activity of human neutrophils. Eur J Immunol. 2007 Feb; 37(2):467-478.
29. van Bruggen R et al., Complement receptor 3, not Dectin-1, is the major receptor on human neutrophils for beta-glucan-bearing particles. Mol Immunol. 2009 Dec; 47(2-3):575-578.
30. Milton D K et al., 2001. Enzyme-linked immunosorbent assay specific for (1-6) branched, (1-3)-β-D-glucan detection in enviormental samples. Appl. Environ. Microbiol. 67: 5420-5424.
31. Bailey R W. The Reaction of Pentoses with Anthrone. Journal of Biological Chemistry, 68:669-672, 1958.
32. Sahu A, Kay B K, Lambris J D: Inhibition of human complement by a C3-binding peptide isolated from a phage-displayed random peptide library. J Immunol 157:884, 1996.
33. Howard J B. Methylamine reaction and denaturation-dependent fragmentation of complement component 3. Comparison with alpha2-macroglobulin. J Biol Chem. 1980 August 10; 255(15):7082-7084.
34. Lepow I H et al., Chromatographic resolution of the first component of human complement into three activities. J Exp Med. 1963 Jun 1; 117:983-1008.
35. Götze O et al., The c3-activator system: an alternate pathway of complement activation. J Exp Med. 1971 Sep 1; 134(3):90-108.
36. Pillemer L et al., The properdin system and immunity. I. Demonstration and isolation of a new serum protein, properdin, and its role in immune phenomena. Science. 1954 Aug 20; 120(3112):279-285.
37. Des Prez R M et al., Function of the classical and alternate pathways of human complement in serum treated with ethylene glycol tetraacetic acid and MgCl2-ethylene glycol tetraacetic acid. Infect Immun. 1975 June; 11(6):1235-1243.
38. Silversmith R E et al., Fluid-phase assembly of the membrane attack complex of complement. Biochemistry. 1986 Feb 25;25(4):841-851.
39. Lavigne L M et al., Beta-glucan is a fungal determinant for adhesion-dependent human neutrophil functions. J Immunol. 2006 December 15; 177(12):8667-8675.
40. Ricklin D et al., Compstatin: a complement inhibitor on its way to clinical application. Adv Exp Med Biol. 2008; 632:273-292.
41. Li B et al., Yeast beta-glucan amplifies phagocyte killing of iC3b-opsonized tumor cells via complement receptor 3-Syk-phosphatidylinositol 3-kinase pathway. J Immunol. 2006 August 1;177(3):1661-1669.
42. Law S K et al., Covalent binding and hemolytic activity of complement proteins. Proc Natl Acad Sci USA. 1980 December; 77(12):7194-7198.
43. Gadjeva M et al., The covalent binding reaction of complement component C3. J Immunol. 1998 Jul 15; 161(2):985-990.
44. Ezekowitz R A et al., Interaction of human monocytes, macrophages, and polymorphonuclear leukocytes with zymosan in vitro. Role of type 3 complement receptors and macrophage-derived complement. J Clin Invest. 1985 December; 76(6):2368-2376.
45. Sahu A et al., Structure and biology of complement protein C3, a connecting link between innate and acquired immunity. Immunol Rev. 2001 April; 180:35-48.
46. Xiong Y M et al., Modulation of CD11b/CD18 adhesive activity by its extracellular, membrane-proximal regions. J Immunol. 2003 July 15; 171(2):1042-1050.
47. Dransfield I et al., Interaction of leukocyte integrins with ligand is necessary but not sufficient for function. J Cell Biol. 1992 March; 116(6):1527-1535.
48. Cai T Q et al., Energetics of leukocyte integrin activation. J Biol Chem. 1995 June 16; 270(24):14358-1465.
49. van Lookeren et al., Macrophage complement receptors and pathogen clearance. Cell Microbiol. 2007 September; 9(9):2095-2102. Epub 2007 June 21.
50. Sutterwala F S et al., Cooperation between CR1 (CD35) and CR3 (CD 11b/CD18) in the binding of complement-opsonized particles. J Leukoc Biol. 1996 June; 59(6):883-890.
51. Rosenthal L A et al., Leishmania major-human macrophage interactions: cooperation between Mac-1 (CD1 lb/CD18) and complement receptor type 1 (CD35) in promastigote adhesion. Infect Immun. 1996 June; 64(6):2206-2215.
52. Cheson B D et al., The role of complement and IgG on zymosan opsonization. Int Arch Allergy Appl Immunol. 1981; 66(1):48-54.
53. Schenkein H A et al., The role of immunoglobulins in alternative complement pathway activation by zymosan. I. Human IgG with specificity for Zymosan enhances alternative pathway activation by zymosan. J Immunol. 1981 January; 126(1):7-10.

54. Wilson M A et al., 1992. Contribution of antibody in normal human serum to early deposition of C3 onto encapsulated and nonencapsulated Cryptococcus neoformans. Infect Immun 60:754-761.
55. Zhang M X et al., 1997. Activation, binding, and processing of complement component 3 (C3) by Blastomyces dermatitidis. Infect. Immun. 65:1849-1855.
56. Zhang M X et al., 2001. Role of glucan and surface protein BAD1 in complement activation by Blastomyces dermatitidis yeast. Infect. Immun. 69:7559-7564.
57. Chiani P et al., Anti-beta-glucan antibodies in healthy human subjects. Vaccine. 2009 Jan 22;27(4):513-519. Epub 2008 Nov 27.
58. Vukajlovich S W. Antibody-independent activation of the classical pathway of human serum complement by lipid A is restricted to re-chemotype lipopolysaccharide and purified lipid A. Infect Immun. 1986 September; 53(3):480-485.
59. Deimann W et al., Hepatic granulomas induced by glucan. An ultrastructural and peroxidase-cytochemical study. Lab Invest. 1980 August; 43(2):172-181.
60. Kilgore et al., Neutrophils and reactive oxygen intermediates mediate glucan-induced pulmonary granuloma formation through the local induction of monocyte chemoattractant protein-1. Lab Invest. 1997 Feb; 76(2):191-201.
61. Cleary J A et al., The effect of molecular weight and beta-1,6-linkages on priming of macrophage function in mice by (1,3)-beta-D-glucan. Immunol Cell Biol. 1999 October; 77(5):395-403.

derived from *Saccharomyces cerevisiae* able to bind to neutrophils and monocytes.

2. The composition of claim 1 wherein the isolated opsonized soluble β-(1,6)-[poly-1,3)-D-glucopyranosyl]-poly-β(1,3)-D-glucopyranose β-glucan comprises an opsonin coupled to the β(1,6)-[poly-1,3)-D-glucopyranosyl]-poly-β(1,3)-D-glucopyranose.

3. The composition of claim 2 wherein the opsonin is covalently coupled to the β(1,6)-[poly-1,3)-D-glucopyranosyl]-poly-β(1,3)-D-glucopyranose.

4. The composition of claim 3 wherein the opsonin is covalently coupled to the β(1,6)-[poly-1,3)-D-glucopyranosyl]-poly-β(1,3)-D-glucopyranose through a conjugation linker.

5. The composition of claim 2 wherein the opsonin comprises C3, C3a, C3b, iC3b, C3bB, C3bBb, C3d, C3dg, C4, C5, C5a, C5b, C6, C7, C8, C9, or any combination of two or more thereof.

6. A composition consisting of:
  isolated iC3b-opsonized soluble β(1,6)-[poly-1,3)-D-glucopyranosyl]-poly-β(1,3)-D-glucopyranose βgulcan derived from *Saccharomyces cerevisiae* able to bind to neutrophils and monocytes.

7. The composition of claim 6 wherein the iC3b is covalently coupled to the soluble β(1,6)-[poly-1,3)-D-glucopyranosyl]-poly-β(1,3)-D-glucopyranose βgulcan.

8. The composition of claim 7 wherein the iC3b is covalently coupled to the soluble β(1,6)-[poly-1,3)-D-glucopyranosyl]-poly-β(1,3)-D-glucopyranose βgulcan through a conjugation linker.

9. The composition of claim 1 wherein the opsonin is covalently coupled to a plurality of soluble β(1,6)-[poly-1,3)-D-glucopyranosyl]-poly-β(1,3)-D-glucopyranose βglucan molecules.

What is claimed is:

1. A composition consisting of:
  isolated opsonized soluble β-(1,6)-[poly-1,3)-D-glucopyranosyl]-poly-β(1,3)-D-glucopyranose β-glucan

* * * * *

SEQUENCE LISTING

```
<160> NUMBER OF SEQ ID NOS: 2

<210> SEQ ID NO 1
<211> LENGTH: 13
<212> TYPE: PRT
<213> ORGANISM: unknown
<220> FEATURE:
<223> OTHER INFORMATION: compstatin polypeptide

<400> SEQUENCE: 1

Ile Cys Val Val Gln Asp Trp Gly His His Arg Cys Thr
1               5                   10

<210> SEQ ID NO 2
<211> LENGTH: 13
<212> TYPE: PRT
<213> ORGANISM: artificial
<220> FEATURE:
<223> OTHER INFORMATION: control polypeptide

<400> SEQUENCE: 2

Ile Ala Val Val Gln Asp Trp Gly His His Arg Ala Thr
1               5                   10
```